(12) United States Patent
Paul et al.

(10) Patent No.: US 7,416,552 B2
(45) Date of Patent: Aug. 26, 2008

(54) MULTIPOLAR, MULTI-LUMEN, VIRTUAL-ELECTRODE CATHETER WITH AT LEAST ONE SURFACE ELECTRODE AND METHOD FOR ABLATION

(75) Inventors: Saurav Paul, Minneapolis, MN (US); Kedar Ravindra Belhe, Minnetonka, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 529 days.

(21) Appl. No.: 11/209,024

(22) Filed: Aug. 22, 2005

(65) Prior Publication Data
US 2007/0078457 A1    Apr. 5, 2007

(51) Int. Cl.
*A61B 18/18* (2006.01)
(52) U.S. Cl. .................... 606/41; 607/105; 607/101
(58) Field of Classification Search .................. 606/41, 606/45, 48–50; 607/101–105
See application file for complete search history.

(56) References Cited

U.S. PATENT DOCUMENTS

| | | | |
|---|---|---|---|
| 4,945,912 A | 8/1990 | Langberg | |
| 5,281,213 A | 1/1994 | Milder et al. | 606/15 |
| 5,281,217 A | 1/1994 | Edwards et al. | 606/41 |
| 5,334,193 A | 8/1994 | Nardella | 606/41 |
| 5,370,644 A | 12/1994 | Langberg | |
| 5,431,649 A | 7/1995 | Mulier et al. | 606/41 |
| 5,433,708 A | 7/1995 | Nichols et al. | 604/113 |
| 5,542,928 A | 8/1996 | Evans et al. | 604/113 |
| 5,584,872 A | 12/1996 | LaFontaine et al. | 607/116 |
| 5,609,151 A | 3/1997 | Mulier et al. | 128/642 |
| 5,658,278 A | 8/1997 | Imran et al. | 606/41 |
| 5,676,693 A | 10/1997 | LaFontaine | 607/116 |
| 5,697,927 A | 12/1997 | Imran et al. | 606/41 |
| 5,725,524 A | 3/1998 | Mulier et al. | 606/41 |
| 5,785,706 A * | 7/1998 | Bednarek | 606/41 |
| 5,876,398 A | 3/1999 | Mulier et al. | 606/41 |
| 5,895,417 A | 4/1999 | Pomeranz et al. | 607/101 |
| 5,913,854 A | 6/1999 | Maguire et al. | 606/41 |
| 5,913,856 A | 6/1999 | Chia et al. | 606/41 |
| 5,919,188 A | 7/1999 | Shearon et al. | 606/41 |
| 5,971,968 A | 10/1999 | Tu et al. | 604/264 |
| 5,997,532 A | 12/1999 | McLaughlin et al. | 606/41 |
| 6,010,500 A | 1/2000 | Sherman et al. | 606/41 |
| 6,015,407 A | 1/2000 | Rieb et al. | 606/41 |
| 6,016,809 A | 1/2000 | Mulier et al. | 128/898 |
| 6,032,077 A | 2/2000 | Pomeranz | 607/101 |

(Continued)

*Primary Examiner*—Michael Peffley
(74) *Attorney, Agent, or Firm*—Heimbecher & Assoc., LLC

(57) ABSTRACT

Multipolar, multi-lumen, virtual-electrode catheters having at least one surface electrode, and methods for treatment (e.g., treatment of cardiac arrhythmias) with such catheters are disclosed. The catheters have at least two internal lumens, and at least one internal, flexible electrode rides in each internal lumen. The flexible electrodes carry treatment energy (e.g., radiofrequency energy). The energy exits the catheters via at least one exit feature (e.g., slots, portholes, or micro-pores). The methods for treatment include operating the catheters in different modes depending upon location and type of treatment to be performed. The treatment energy delivered by one of the internal, flexible electrodes may be directed to the other internal, flexible electrode; or the energy delivered by one or both of the internal, flexible electrodes may be directed to one or more surface electrodes. The delivered energy establishes at least one electric field, and possibly one or more lesions, in the tissue.

37 Claims, 11 Drawing Sheets

U.S. PATENT DOCUMENTS

| | | | |
|---|---|---|---|
| 6,063,080 A | 5/2000 | Nelson et al. | 606/41 |
| 6,068,653 A | 5/2000 | LaFontaine | 607/116 |
| 6,080,151 A * | 6/2000 | Swartz et al. | 606/45 |
| 6,119,041 A | 9/2000 | Pomeranz et al. | 607/101 |
| 6,120,476 A | 9/2000 | Fung et al. | 604/95 |
| 6,120,500 A | 9/2000 | Bednarek et al. | 606/41 |
| 6,132,426 A | 10/2000 | Kroll | 606/41 |
| 6,168,594 B1 | 1/2001 | LaFontaine et al. | 606/41 |
| 6,217,576 B1 | 4/2001 | Tu et al. | 606/41 |
| 6,219,582 B1 | 4/2001 | Hofstad et al. | 607/122 |
| 6,235,022 B1 | 5/2001 | Hallock et al. | 606/41 |
| 6,235,044 B1 | 5/2001 | Root et al. | 606/200 |
| 6,238,393 B1 | 5/2001 | Mulier et al. | 606/41 |
| 6,241,722 B1 | 6/2001 | Dobak et al. | 606/23 |
| 6,409,722 B1 | 6/2002 | Hoey et al. | 606/34 |
| 6,454,766 B1 | 9/2002 | Swanson et al. | 606/41 |
| 6,605,087 B2 | 8/2003 | Swartz et al. | 606/41 |
| 6,702,811 B2 | 3/2004 | Stewart et al. | |
| 6,717,275 B2 | 4/2004 | Webster, Jr. | 604/20 |
| 6,858,026 B2 | 2/2005 | Sliwa et al. | 606/28 |
| 6,960,207 B2 * | 11/2005 | Vanney et al. | 606/41 |
| 7,179,257 B2 * | 2/2007 | West et al. | 606/41 |
| 2004/0181189 A1 | 9/2004 | Roychowdhury et al. | |
| 2005/0055019 A1 | 3/2005 | Skarda | |
| 2007/0027448 A1 * | 2/2007 | Paul et al. | 606/41 |

\* cited by examiner

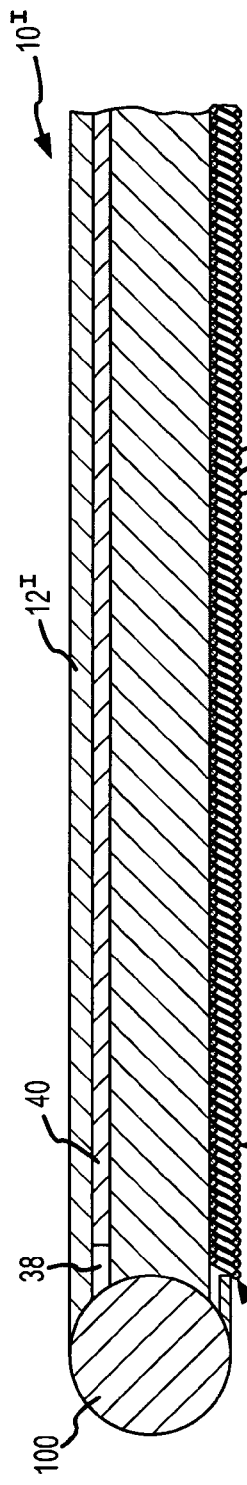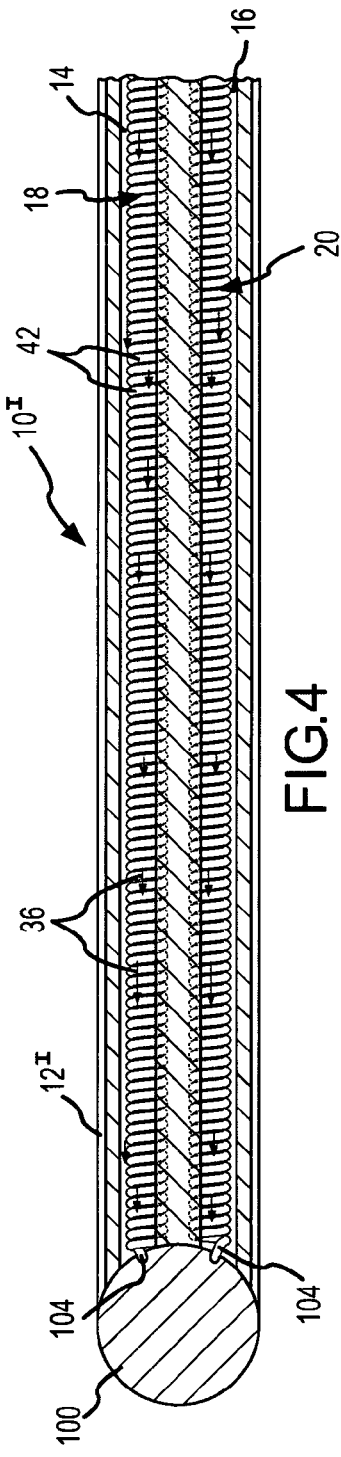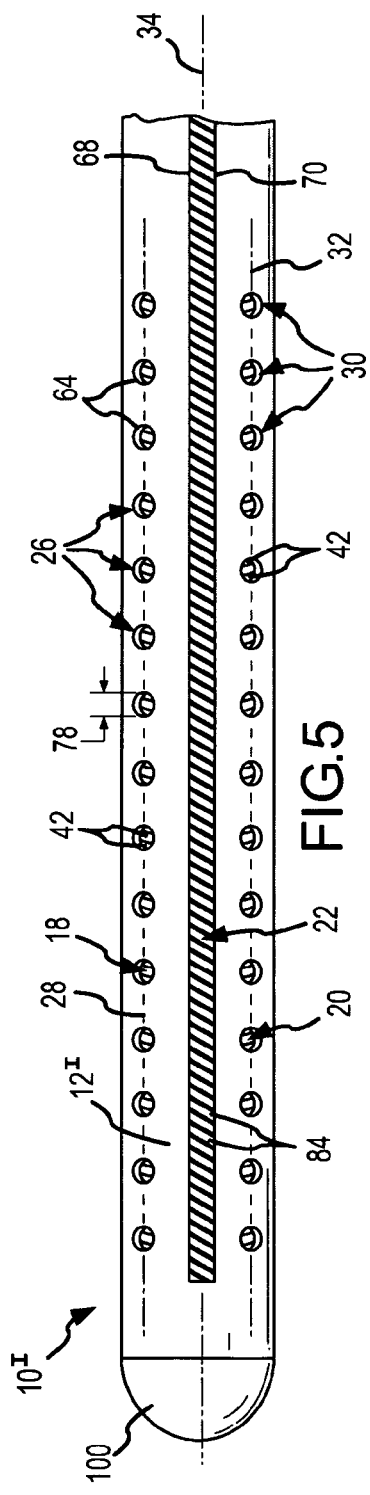

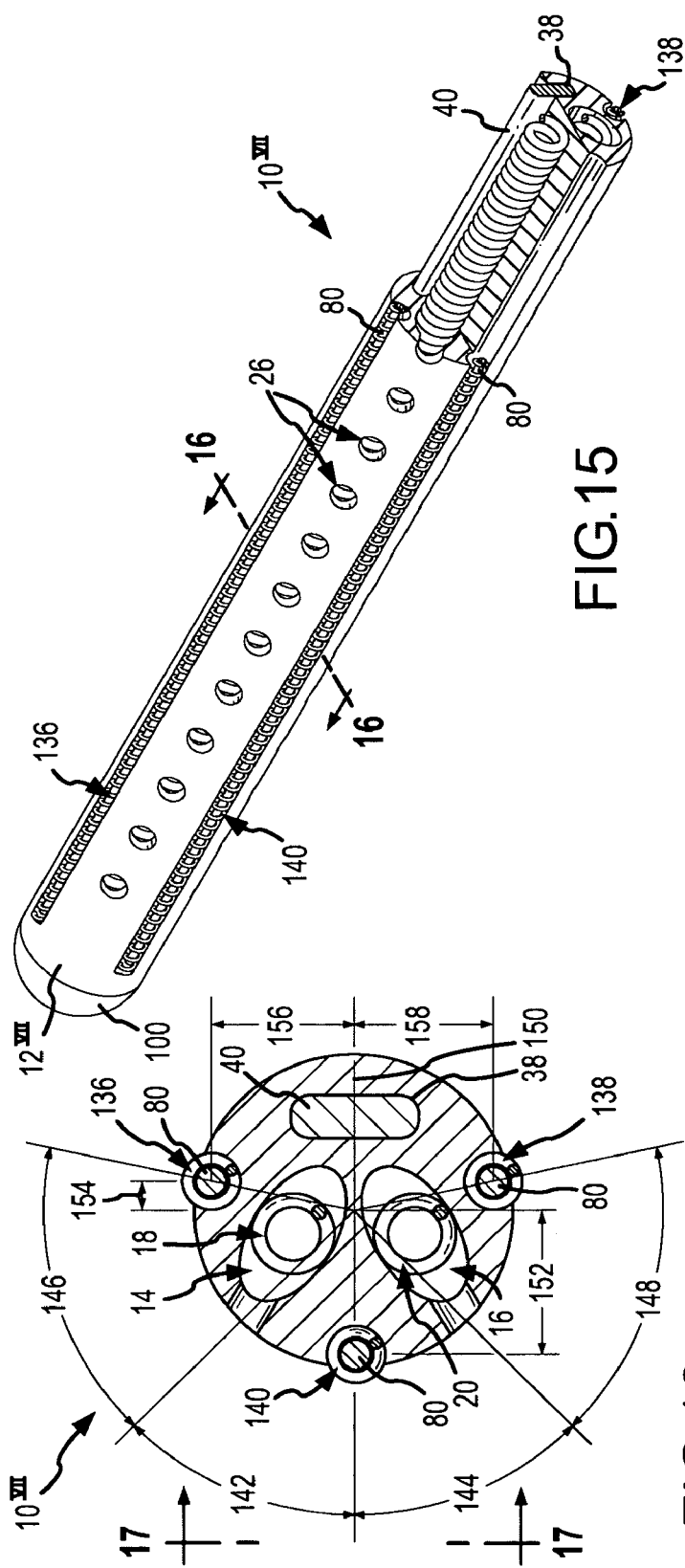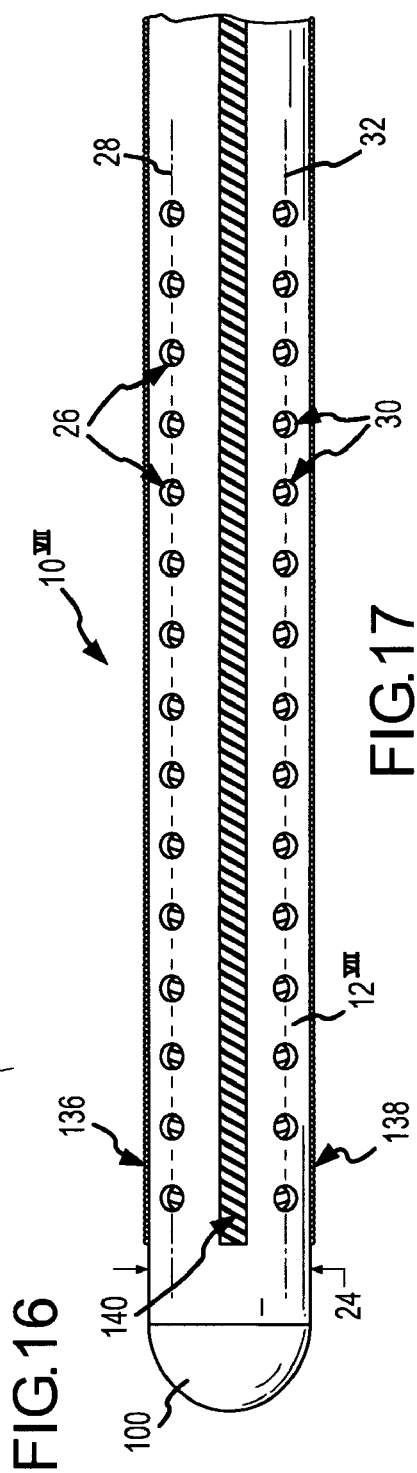

MULTIPOLAR, MULTI-LUMEN, VIRTUAL-ELECTRODE CATHETER WITH AT LEAST ONE SURFACE ELECTRODE AND METHOD FOR ABLATION

BACKGROUND OF THE INVENTION a. Field of the Invention

The instant invention is directed toward virtual-electrode catheters and to methods for using such virtual-electrode catheters. More specifically, it relates to multipolar, multi-lumen virtual-electrode catheters having at least two internal electrodes and at least one surface electrode, and to methods of using these catheters for treatment of cardiac arrhythmias via, for example, radiofrequency (RF) ablation.

b. Background Art

Conventional catheter techniques of RF ablation for treating cardiac arrhythmias use RF electrodes in a unipolar mode. In this mode, only the active RF electrodes are placed at the site of the ablation. The dispersive electrodes are placed at locations remote from the ablation site, typically on the skin of the patient.

In the unipolar mode, the RF current decreases as $1/r^2$, and the RF energy decreases as $1/r^4$, where "r" is the radial distance from an active electrode of a catheter. Because tissue ablation is caused by RF energy deposition into the tissue, the depth of the ablation is limited to a narrow rim around the catheter electrode. Increased lesion depth, therefore, requires high power. High power, however, causes rapid temperature increases and potential "hot-spots" at the electrode-tissue interface.

The virtual electrode technique mitigates this problem of temperature increases at the electrode-tissue interface by using cooled conductive fluid flowing onto the tissue surface. The fluid flow rate necessary to provide adequate surface cooling depends upon the RF power being delivered. The higher the power, the higher the flow rate that is necessary. To create lesions 3-4 mm deep using existing devices may require 50 watts for 60 seconds and a fluid flow rate of 72 ml per minute. For a full-circumferential lesion, these same existing devices require a minimum of two separate procedures at these settings. The minimum RF energy delivered during the 120 seconds total duration is, therefore, 6000 Joules; and the total volume of fluid delivered is over 140 ml. By contrast, for a typical pulmonary vein of 22 mm diameter, a lesion size of 60 mm×3 mm×3 mm obtained with a temperature rise of 50° C. requires a total energy of only about 120 Joules. This means that only 2% of the applied RF energy is used to create the lesion. The remaining 98% of the applied energy is lost to heating other substances such as the infused fluid, the catheter body, surrounding tissue, blood, and other tissue fluids. Existing techniques can be, therefore, highly inefficient.

BRIEF SUMMARY OF THE INVENTION

It is desirable to be able to improve the efficiency of ablation, including RF ablation using virtual-electrode technology. Accordingly, it is an object of the disclosed invention to provide an improved ablation catheter and method for treatment of, for example, cardiac arrhythmias.

In one form, the present invention comprises a multipolar, multi-lumen, virtual-electrode catheter for treatment of tissue. The catheter comprises a catheter body having an outer surface; a first sidewall; a second sidewall; a first longitudinally-extending internal lumen, extending adjacent to the first sidewall and adapted to transport conductive fluid; and a second longitudinally-extending internal lumen, extending adjacent to the second sidewall and adapted to transport conductive fluid. The catheter in this for also comprises a first exit feature extending through the first sidewall of the catheter body, wherein the first exit feature thereby fluidly couples the first internal lumen to the outer surface of the catheter body; a second exit feature extending through the second sidewall of the catheter body, wherein the second exit feature thereby fluidly couples the second internal lumen to the outer surface of the catheter body; a first internal electrode residing within at least a distal portion of the first internal lumen and adapted to deliver treatment energy to the tissue via the conductive fluid and the first exit feature; a second internal electrode residing within at least a distal portion of the second internal lumen and adapted to deliver treatment energy to the tissue via the conductive fluid and the second exit feature; and at least one surface electrode mounted on the outer surface of the catheter body adjacent to the first and second exit features. The internal electrodes may be, for example, coil electrodes, wire strand electrodes, and or tubular electrodes. The surface electrode or electrodes may be, for example, a conductive coil or a conductive tube and may be mounted in and retained by a longitudinally-extending, C-shaped channel on the outer surface of the catheter body. Each of the first and second exit features may be, for example, a plurality of exit portholes, at least one exit slot, and a plurality of micro-pores. One or more temperature sensors (e.g., thermocouples, thermisters, or fiber optic sensors) may be associated with the surface electrode or electrodes.

In another form, the invention comprises multipolar, multipolar, multi-lumen, virtual-electrode catheter for performing radiofrequency ablation of cardiac tissue. In this form, the catheter comprises (1) a catheter body defining an outer surface, a first internal lumen, and a second internal lumen, wherein the first and second internal lumens are adapted to carry conductive fluid; (2) at least three metal electrodes positioned on the outer surface of the catheter body, wherein the at least three metal electrodes are adapted for placement against the cardiac tissue; (3) a first metal conductor positioned within the first internal lumen and adapted to impart radiofrequency energy to the conductive fluid; (4) a second metal conductor positioned within the second internal lumen and adapted to impart radiofrequency energy to the conductive fluid; (5) a first opening on the outer surface of the catheter, the first opening adapted to create a flow path for the conductive fluid in the first internal lumen to flow out of the catheter and impinge upon the cardiac tissue as a virtual-electrode; (6) a second opening on the outer surface of the catheter, the second opening adapted to create a flow path for the conductive fluid in the second internal lumen to flow out of the catheter and impinge upon the cardiac tissue as a virtual-electrode; and (7) at least one temperature sensor on the outer surface of the catheter body in close juxtaposition to at least one of the at least three metal electrodes. The three metal electrodes positioned on the outer surface of the catheter body may include a first outboard surface electrode, a second outboard surface electrode, and an intermediate surface electrode. The first outboard surface electrode and the intermediate surface electrode may straddle the first opening on the outer surface of the catheter, and the second outboard surface electrode and the intermediate surface electrode may straddle the second opening on the outer surface of the catheter.

In yet another form, the present invention comprises a method for tissue ablation using a multipolar, multi-lumen, virtual-electrode catheter. The catheter used to carry out this method may comprise, for example, (1) a catheter body with a sidewall and an outer surface; (2) a first internal lumen extending within the catheter body and adapted to flowingly receive a conductive fluid; (3) a second internal lumen extending within the catheter body and adapted to flowingly receive the conductive fluid; (4) a first exit feature comprising a flow path from the first internal lumen through the catheter body sidewall to the catheter outer surface, the first exit feature being adapted to permit the conductive fluid to exit from the first internal lumen toward the tissue; (5) a second exit feature comprising a flow path from the second internal lumen through the catheter body sidewall to the catheter outer surface, the second exit feature being adapted to permit the conductive fluid to exit from the second internal lumen toward the tissue; (6) a first internal flexible conductor mounted within the first internal lumen adjacent to the first exit feature and to a first inner surface of the catheter body sidewall, wherein the first internal flexible conductor is adapted to deliver ablation energy to the tissue via the conductive fluid in the first internal lumen; (7) a second internal flexible conductor mounted within the second internal lumen adjacent to the second exit feature and to a second inner surface of the catheter body sidewall, wherein the second internal flexible conductor is adapted to deliver ablation energy to the tissue via the conductive fluid in the second internal lumen; and (8) at least one surface electrode mounted on the outer surface of the catheter body adjacent to at least one of the first and second exit features. The method comprises the steps of (a) flowing the conductive fluid within the first and second internal lumens and out of the first and second exit features; (b) delivering ablation energy to the first and second internal flexible conductors; (c) generating an electric field between at least one of the first and second internal flexible conductors and the at least one surface electrode; and (d) terminating delivery of the ablation energy upon creating of a lesion in the tissue.

In another form, the present invention comprises a method for tissue ablation using a multipolar, multi-lumen, virtual-electrode catheter. The method comprises the following steps: (a) placing against the tissue at least one of a first outboard dispersive surface electrode, a second outboard dispersive surface electrode, and an intermediate dispersive surface electrode, wherein the first outboard dispersive surface electrode, the second outboard dispersive surface electrode, and the intermediate dispersive surface electrode are each mounted on an outer surface of a catheter body of the virtual-electrode catheter; (b) flowing a conductive fluid through a first internal lumen and a second internal lumen, both the internal lumens extending within the catheter body toward at least one exit feature that is adjacent to at least one of the first outboard dispersive surface electrode, the second outboard dispersive surface electrode, and the intermediate dispersive surface electrode; (c) delivering ablation energy to at least one of a first active internal flexible conductor within the first internal lumen, and a second active internal flexible conductor within the second internal lumen; (d) generating at least one concentrated electric field between at least one of the first and second internal flexible conductors, and at least one of the first outboard dispersive surface electrode, the second outboard dispersive surface electrode, and the intermediate dispersive surface electrode; and (e) terminating delivery of the ablation energy after creation of a lesion in the tissue.

In yet another form, the present invention comprises a method for tissue ablation using a multipolar, multi-lumen, virtual-electrode catheter. In this for, the method comprises the steps of setting up a first virtual electrode comprising an ablative energy source, a first internal electrode, a first exit feature, and conductive fluid flowing along the first internal electrode and through the first exit feature; setting up a second virtual electrode comprising the ablative energy source, a second internal electrode, a second exit feature, and conductive fluid flowing along the second internal electrode and through the second exit feature; placing each of a first outboard surface electrode, a second outboard surface electrode, and an intermediate surface electrode against tissue to be ablated; activating the first virtual electrode to establish a first electric field and a second electric field in the tissue; activating the second virtual electrode to establish a third electric field and a fourth electric field in the tissue; and maintaining at least one of the first, second, third, and fourth electric fields until a lesion is created in the tissue. The first electric field may extend between the first exit feature and the first outboard surface electrode. The second electric field may extend between the first exit feature and the intermediate surface electrode. The third electric field may extend between the second exit feature and the intermediate surface electrode. The fourth electric field may extend between the second exit feature and the second outboard surface electrode.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 3 is a cross-sectional view taken along line 3-3 of FIG. 2.

FIG. 4 is a cross-sectional view taken along line 4-4 of FIG. 2.

FIG. 5 is a front elevation of the embodiment depicted in FIGS. 1-4 taken in the direction of line 5-5 of FIG. 2.

FIG. 15 is similar to FIG. 1, but depicts a fragmentary, isometric view of a multipolar, multi-lumen, virtual-electrode catheter according to a seventh embodiment of the present invention, with a portion of the catheter body broken-away to reveal various internal features.

FIG. 16 is a cross-sectional view taken along line 16-16 of FIG. 15.

FIG. 17 is a front elevation of the embodiment depicted in FIGS. 15 and 16 taken in the direction of line 17-17 of FIG. 16.

DETAILED DESCRIPTION OF THE INVENTION

Several embodiments of the distal portion of multipolar, multi-lumen, virtual-electrode catheters (e.g., $10^I$ in FIGS. 1-5) according to the present invention are disclosed. In general, each virtual-electrode catheter according to the present invention comprises a catheter body (e.g., $12^I$ in FIG. 1) having a plurality of internal lumens (e.g., 14, 16 in FIG. 2) extending through it, with internal flexible current carriers or electrodes (e.g., 18, 20 in FIG. 2) mounted in the internal lumens, and at least one surface electrode (e.g. 22 in FIGS. 1 and 2) on the outer surface of the catheter. Details of the various embodiments of the present invention are described below with specific reference to the figures.

Figure 1:
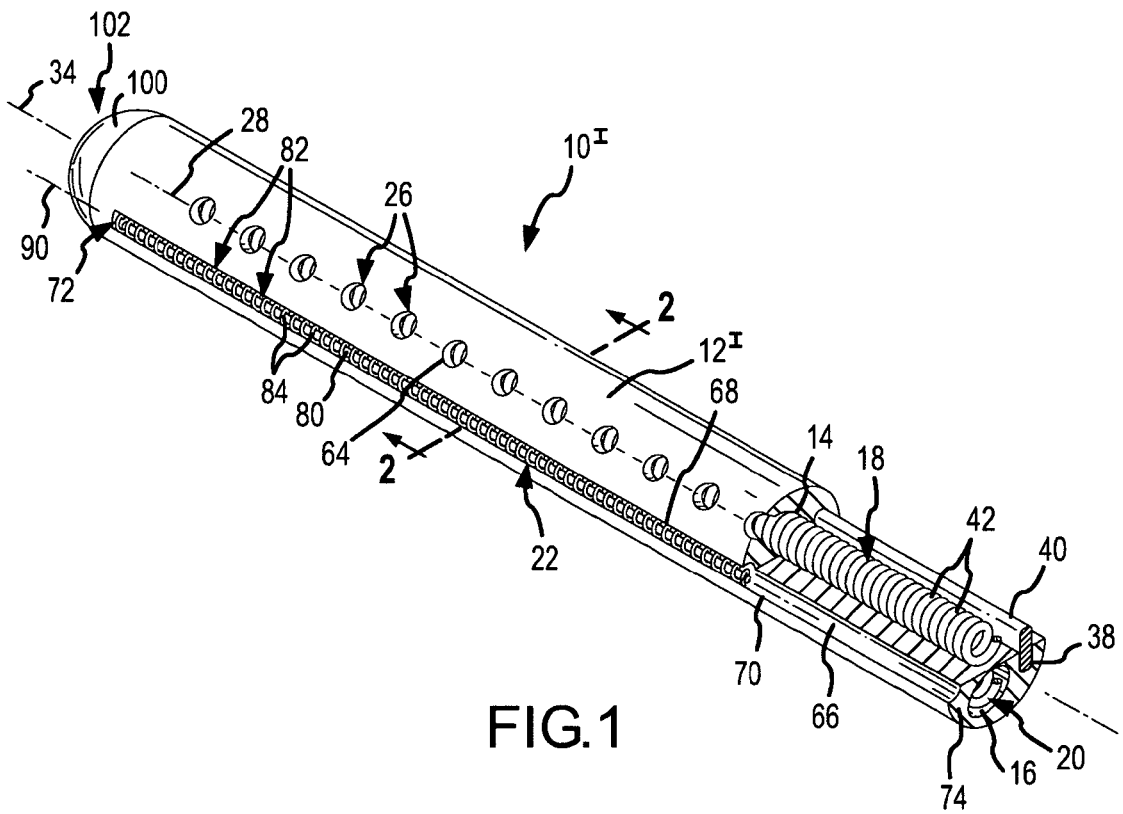
FIG. 1 is a fragmentary, isometric view of a multipolar, multi-lumen, virtual-electrode catheter according to a first embodiment of the present invention with a portion of the catheter body broken-away to reveal various internal features.
Figure 2:
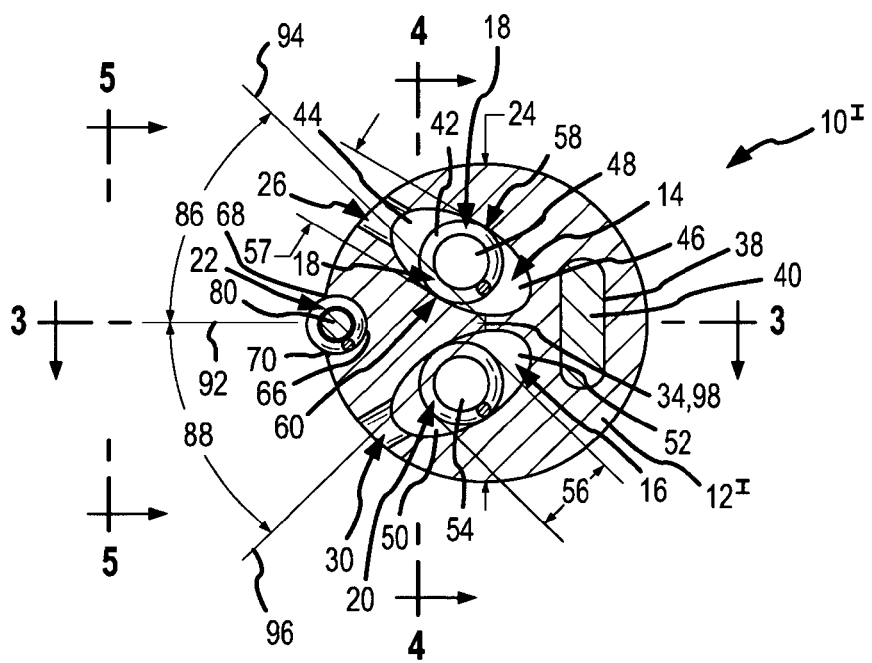
FIG. 2 is a cross-sectional view taken along line 2-2 of FIG. 1.

FIGS. 1-5 depict a distal portion 101 of a multipolar, multi-lumen virtual-electrode catheter according to a first embodiment of the present invention. The catheter comprises a catheter body $12^I$. As shown in FIG. 2, in this first embodiment of the multipolar, multi-lumen virtual-electrode catheter, the catheter body $12^I$ has a circular cross section that is relatively small. For example, the catheter body may have a diameter 24 of 0.091 inches (approximately 2.31 mm). Clearly, this particular diameter for the catheter body is not required; and the multipolar, multi-lumen virtual-electrode catheter according to the present invention may be sized as required to fit, for example, specific vascular or other body cavities.

As shown in FIGS. 1, 2, and 5, an exit feature extends through a sidewall of the catheter body. In particular, the exit feature in this first embodiment comprises a first plurality of exit portholes or nozzles 26 that are arranged along a first longitudinally-extending porthole centerline 28 along the surface of the catheter body $12^I$, and a second plurality of exit portholes or nozzles 30 that are arranged along a second longitudinally-extending porthole centerline 32 along the surface of the catheter body. As best seen by looking at FIGS. 2 and 5, these exit portholes 26, 30 extend through the sidewall of the catheter body $12^I$. In the depicted embodiment, as shown to good advantage in FIG. 2, the exit portholes 26, 30 extend radially through the sidewall relative to a catheter longitudinal axis 34.

The catheter body $12^I$ includes at least two longitudinally-extending internal lumen 14, 16, and an internal flexible current carrier or conductor 18, 20 is mounted in each internal lumen 14, 16. In the embodiment depicted in FIGS. 1-5, the internal lumens have an elliptical cross section, which, among other advantages mentioned below, helps direct fluid 36 (e.g., FIG. 4) toward the exit portholes 26, 30, but the internal lumens need not have an elliptical cross section. The elliptical cross-sectional configuration efficiently moves a high volume of fluid 36 in a more compact configuration. The catheter body $12^I$ of this embodiment also comprises an optional, third lumen or rail lumen 38 in which a shape-retention or shape-creating rail or wire 40 is mounted (e.g., a nickel-titanium wire, which is also know as NiTi or Nitinol wire). This rail or wire helps with steering and shaping the distal portion of the catheter.

In this first embodiment $10^I$ of the present invention, each internal flexible electrode 18, 20 comprises a single, large, internal coil electrode. As shown to good advantage in FIGS. 1 and 4, desirably these internal coil electrodes 18, 20 have a tight spring pitch (i.e., tightly wound coils 42) with individual coils that are closely packed (e.g., 2-3 turns between adjacent portholes or approximately ¹⁄₁₀₀₀th of an inch between coils). The individual coils or turns 42 of each large internal coil electrode 18, 20 permit fluid 36 flowing through the elliptical internal lumen 14, 16 to pass between the coils or turns 42 comprising the electrode before exiting from the catheter via the exit portholes 26, 30. These tightly wound coils help regulate fluid flow within the internal lumens 14, 16 of the catheter body and out of the exit portholes 26, 30. In FIG. 5, the individual turns 42 of the larger internal coil electrodes 18, 20 are visible through the exit portholes 26, 30. The large internal coil electrodes stretch and relax and are put under tension and compression as the distal portion $10^I$ of the multipolar, multi-lumen virtual-electrode catheter is manipulated during use of the device. As the coils thus flex and contort, the gaps between adjacent coils may change in size slightly. This may create some pressure gradients in the flow distribution along the plurality of exit portholes, which may affect the impedance and heating of the conductive fluid 36 (i.e., the cooling fluid) flowing in the internal lumens 14, 16 of the catheter.

Since the internal flexible electrodes 18, 20 depicted in the embodiment $10^I$ of FIGS. 1-5, are large coils having annular cross sections, when these large coils are mounted in their respective elliptical internal lumens 14, 16, first and second flow channels are defined. As shown to best advantage in FIG.

2, the first flow channel comprises a first forward crescent-moon-shaped region 44, a first rearward crescent-moon-shaped region 46, and a first circular central region 48; and the second flow channel comprises a second forward crescent-moon-shaped region 50, a second rearward crescent-moon-shaped region 52, and a second circular central region 54. In particular, each large coil electrode 18, 20 is sized such that its outside diameter 56 is approximately the same length as the length 57 of the minor axis of the elliptical cross section of the internal lumen 14 or 16 in which it is mounted. Thus, each large coil electrode 18, 20 extends from the top 58 to the bottom 60 of the elliptical internal lumen (FIG. 2) in which it is mounted, across the internal lumen's minor axis. In this particular configuration, each large internal coil's position relative to the elliptical internal lumen, and thus relative to the exit portholes or nozzles, remains relatively unchanged even when the distal portion of the multipolar, multi-lumen virtual-electrode catheter is bent or curved during manipulation of the catheter during use. In other words, although the distal portion of the multipolar, multi-lumen virtual-electrode catheter depicted in all of the figures is shown as straight for simplicity, the catheter may be precurved for a particular application and/or the catheter may be curveable or shapeable during use by manipulation of, for example, the rail 40 visible in, for example, FIGS. 1-3. Nevertheless, in this depicted embodiment, the large coil electrodes 18, 20 remain relatively fixed within their internal lumens 14, 16, respectively.

Each internal flexible electrode may alternatively comprise a straight length of flexible solid wire (not shown) rather than a coiled wire. This type of internal flexible electrode may, however, have a few drawbacks. For example, if each internal flexible electrode comprises a solid wire having an annular or circular cross section, and if that cross section has an outer diameter equal to the length of the minor axis of the internal lumen's elliptical cross section, any fluid flowing in the rearward crescent-moon-shaped region or flow channel (e.g., 46 in FIG. 2) would be inhibited or prohibited from reaching the exit portholes 26, 30. On the other hand, if the internal flexible electrode comprises a wire of a diameter that does not match the length of the minor axis of the internal lumen's elliptical cross section, the wire may shift relative to the exit portholes during manipulation of the multipolar, multi-lumen virtual-electrode catheter. For example, bending the catheter to form a curve may place part of the wire closer to some of the exit portholes than others, which may undesirably alter the virtual-electrode effects longitudinally along the distal portion of the multipolar, multi-lumen virtual-electrode catheter. In other words, this shifting can lead to undesirable variations and concomitant unpredictability in the energy delivered via the virtual-electrode catheter during use.

As alluded to above, a shape-retention or shape-forming rail or wire 40 (e.g., a NiTi wire) may be present. In particular, as shown in FIGS. 1-3, the catheter body may comprise the third lumen 38, which extends longitudinally through the catheter body 12' and accommodates this wire or rail 40. In the depicted embodiment 10', the wire or rail 40 has a rounded-rectangular cross-sectional configuration that is "keyed" to, or that complements, the cross-sectional configuration of the third lumen 38 (see FIGS. 1-3). When present, this wire or rail can perform different functions. For example, the wire or rail may be "biased or preset" to take a desired curvature. In particular, the wire or rail may be preset to force the distal portion 10' of the multipolar, multi-lumen virtual-electrode catheter into a particular curvature. Thus, once the catheter has been delivered, using an introducer or other catheter (not shown), adjacent to tissue 62 to be diagnosed or treated (see, e.g., FIG. 22), the distal portion 10' of the catheter is extended past the distal end of the introducer or other catheter that delivered the virtual-electrode catheter to the tissue 62 to be treated. Once the distal portion of the multipolar, multi-lumen virtual-electrode catheter is extended out of the delivery device, the wire or rail 40 would cause the distal portion 10' of the multipolar, multi-lumen virtual-electrode catheter to assume the desired configuration. In this manner, an ultimately curved distal portion may be delivered to a treatment or diagnosis site prior to taking its curved configuration. Alternatively, the wire or rail 40 may be connected to some type of control handle, steering handle, or other device (not shown) that remains external to a patient, whereby manipulation of this control handle, steering handle, or other device allows a physician to manipulate the shape and placement of the distal portion 10' of the catheter.

As shown to best advantage in FIG. 4, conductive fluid or suspension 36 flows substantially longitudinally through the elliptical internal lumens 14, 16, along and around the large internal coil electrodes 18, 20. As used herein, "suspension" means a mixture that may comprise particles, fluids, or other materials added to a base fluid to adjust the electrical or other properties of the base fluid. Eventually, the conductive fluid or suspension 36 is delivered to the tissue 62 under treatment (see FIGS. 22-27, which schematically depict conductive fluid 36 oozing from the tissue-catheter interface). As explained further below, during an ablation procedure, that tissue would be against or next to the outside surface of the distal portion of the multipolar, multi-lumen virtual-electrode catheter, adjacent to the annular outer edges 64 of the exit portholes 26, 30. The large internal coils 18, 20 thus are able to deliver energy (e.g., RF energy) to the tissue 62.

Since the present invention preferably operates in a multipolar mode, the device further comprises at least one surface electrode in addition to the internal flexible electrodes. In the first embodiment of the present invention, which is depicted in FIGS. 1-5, the surface electrode 22 comprises a single coil of conductive material (e.g., metal, conductive silicon, or conductive polymer), which may be seen in FIGS. 1, 2, 3, and 5. The coil may be hollow (i.e., the wire wound into the coil may be a hollow-core or tubular wire). This "hollow coil" alternative embodiment is not shown in the figures. In the embodiment depicted in FIGS. 1-5, the surface coil electrode 22 is mounted in a longitudinally-extending, C-shaped channel 66 on the surface of the distal portion 10' of the multipolar, multi-lumen virtual-electrode catheter. As shown to good advantage in FIGS. 1 and 2, this longitudinally-extending channel 66 has a C-shaped cross section in this embodiment, wherein a top edge 68 and a bottom edge 70 of the "C" retain the surface electrode 22 in the channel 66. The surface electrode 22, in this embodiment, may be mounted in the channel 66 by, for example, inserting a longitudinal end 72 of the surface electrode into the channel 66 starting from an end of the C-shaped channel 66.

For example, if, in the embodiment as depicted in FIG. 1, the C-shaped channel 66 terminates at end surface 74, the surface electrode 22 could be inserted into the C-shaped channel 66 from right to left in the drawing of FIG. 1. Subsequently, the distal portion 10' may be mounted (e.g., by adhesion) to a section of catheter shaft (not shown) by adhering the surface 74 depicted in FIG. 1 to a complementary surface on a distal end of the portion of catheter shaft (not shown) that will be used to manipulate the distal portion 10' of the multipolar, multi-lumen virtual-electrode catheter into position.

The elliptical lumens 14, 16 facilitate heat dissipation when the surface electrode 22 and/or the internal electrodes 18, 20 heat during use of the catheter for an ablation procedure. In particular, the elliptical lumens make it possible for the material comprising that part of the catheter body adjacent to where the internal coil electrodes contact the internal lumen sidewalls to be relatively thick, which facilitates better heat dissipation.

As explained further below, in the first embodiment of the present invention (FIGS. 1-5), the large internal coils 18, 20 act as the active electrodes. In particular, the large internal coils 18, 20 may be activated one at a time (e.g., one of the electrodes may be activated continuously or intermittently), they may be activated alternatingly (e.g., one electrode may be activated and then the other may be activated), or they may be activated simultaneously (e.g., both electrodes may be activated at the same time continuously or intermittently). Thus, the large internal coils 18, 20 would be connected to, for example, an RF current source (not shown) outside of the patient's body via one or more conductors extending longitudinally through the catheter shaft to a proximal portion of the catheter shaft that remains outside of the patient's body. The small coil surface electrode 22 serves as a dispersive electrode when the catheter is used in a multipolar mode, and would be connected to the return end of the RF source in this mode. The surface electrode coil 22 thus acts as an inactive return electrode. In other words, during operation of the catheter according to the present invention in its multipolar mode, RF energy (or some other type of energy) may be delivered to one or both of the large internal coils 18, 20, and then exit from the exit portholes 26, 30 via conductive fluid 36 flowing through and around the active, large internal coil or coils (e.g., FIG. 4). This RF energy is then "captured" or returned by the surface electrode coil 22 to the RF generator or ground, which creates an electric field (see, e.g., 162, 164, 168 in FIGS. 22-24) between the large internal coil (or coils) and the surface electrode coil (or coils) in the tissue 62 adjacent to the exit portholes 26, 30 and adjacent to the surface electrode coil 22.

When the first embodiment, which is depicted in FIGS. 1-5, is operated in a first mode, the RF energy exits one or both of the internal lumens 14, 16 via the exit portholes 26, 30 before traveling to the surface electrode 22. The exit portholes are thus sized and spaced appropriately (see, for example, US patent application publication no. US 2004/0143253 A1, which is hereby incorporated by reference as though fully set forth herein). The exit portholes 26, 30, which are distributed along the porthole centerlines 28, 32, respectively, are configured to create "nozzle effects" with minimum pressure loss. If the exit portholes or nozzles are too large, an inordinate or undesirable amount of conductive fluid 36 may be delivered to the patient's bloodstream 76 (see, e.g., FIGS. 22-27, which schematically depict a patient's bloodstream 76 flowing adjacent to the tissue 62 being treated) and the electric field that is desirably established in the tissue may be "washed away." If, on the other hand, the exit portholes 26, 30 are too small, electrical resistance may exceed desirable levels, making it difficult to deliver the desired amount of ablation energy to the tissue 62 to be treated. The diameter 78 (FIG. 5) of the exit portholes 26, 30 may be, for example, 0.012 inches (i.e., approximately 0.30 mm).

A thermal sensor may be mounted adjacent to the surface electrode 22. In the particular embodiment depicted in FIGS. 1-5, for example, a longitudinally-extending thermal sensor 80 extends within the surface electrode coil 22. This thermal sensor 80 may be any type of temperature sensor (e.g., a thermocouple, a thermister, or a fiber optic sensor). Since, in this embodiment, the surface electrode 22 is not actively cooled, having a thermal sensor 80 placed in close juxtaposition to the external, surface electrode 22, makes it possible to monitor when the surface electrode may be approaching undesirably high temperatures. If the surface electrode were to become too hot, coagulum may be formed in the gaps 82 between the individual coils 84 of the surface electrode 22 causing performance degradation and possibly other complications. As previously mentioned, the surface electrode coil may be formed from a hollow wire. If the surface electrode coil were constructed from such a hollow wire, a cooling fluid may be pumped through the hollow wire to help regulate the temperature of the surface electrode.

Desirably, the surface area of the surface electrode is selected so that the surface electrode can handle the energy being delivered to it by one or both of the internal coil electrodes 18, 20 via the conductive saline 36. Also, the surface area of the surface electrode may be configured so that energy may be delivered in reverse, that is, from the surface electrode 22 to one or both of the internal coil electrodes 18, 20.

Referring most specifically to FIG. 2, the radial offset angles 86, 88 between the surface electrode 22 and each row of exit portholes 26, 30 is another consideration. In particular, a first radial offset angle 86 is present between the longitudinal axis of the surface electrode 90 and the first longitudinally-extending porthole centerline 28 (see FIGS. 1, 2, and 5); and a second radial offset angle 88 is present between the longitudinal axis 90 of the surface electrode 22 and the second longitudinally-extending porthole centerline 32 (see FIGS. 2 and 5). Both of these radial offset angles 86, 88 are measured between radial lines 92, 94, 96 that extend from a vertex 98 on the catheter longitudinal axis 34. In the embodiment depicted in FIGS. 1-5, the first radial offset angle 86 is the same as the second radial offset angle 88. It may be beneficial for certain applications for the first radial offset angle to be different from the second radial offset angle.

The offset angles 86, 88 (see FIG. 2) between the radial lines 94, 96 passing through the centerlines 28, 32 (see FIGS. 1, 2, and 5), respectively, of the exit portholes 26, 30, respectively, and the radial line 92 (see FIG. 2) passing through the longitudinally-extending axis 90 (see FIG. 1) of the surface electrode 22 (i.e., the angular displacements 86, 88 of the longitudinal centerline 90 of the surface electrode 22 relative to the longitudinal centerlines 28, 32 of the exit portholes) may be, for example, 45°. When both radial offset angles 86, 88 are approximately 45°, the active electrodes 18, 20 and the dispersive electrode are relatively close to each other. By placing the active electrodes and the dispersive electrode 22 sufficiently close to each other, it is possible to provide high current density and a highly-localized electric field within the tissue 62 (see, e.g., FIGS. 22-24) contacting the distal portion of the multipolar, multi-lumen virtual-electrode catheter adjacent to the exit portholes 26, 30 and adjacent to the surface electrode 22. In one example, the multipolar, multi-lumen, virtual-electrode catheter has the circular cross section depicted in FIGS. 1 and 2, and the diameter 24 (FIG. 2) of that circular cross section is approximately 0.091 inches (i.e., approximately 2.31 mm), and the outside diameter of the large internal coil is 0.024 inches (i.e., approximately 0.61 mm).

If the offset angles 86, 88 are too small or acute, no energy (or an undesirably low amount of current) may pass through the tissue 62 (visible in, e.g., FIGS. 22-27), and the energy may predominately pass directly from the exit portholes 26, 30 to the surface electrode 22, with an undesirably small amount of energy passing through the tissue 62. Alternatively, if the offset angles 86, 88 are too large, the electric field may become undesirably attenuated. In this latter case, the multipolar, multi-lumen virtual-electrode catheter effectively acts as a unipolar, virtual-electrode catheter.

As shown to good advantage in FIGS. 3 and 4, the distal portion 10$^I$ of the multipolar, multi-lumen virtual-electrode catheter may comprise a terminal sphere or ball 100 at its distal end 102. This terminal sphere 100, which may be solid or hollow, may also be used to stabilize the internal electrodes 18, 20. In the depicted embodiment, for example, each large internal coil includes a distal projection or anchor 104. Each of these distal projections 104 can comprise a short section at the extreme distal end of one of the large internal coils 18, 20 that is mounted in or otherwise affixed to the terminal sphere 100. The anchored distal projections 104 help keep the large internal coils 18, 20 from floating or shifting around undesirably and, thus, helps to ensure that the large internal coils extend over all of the exit portholes 26, 30.

Figure 6:
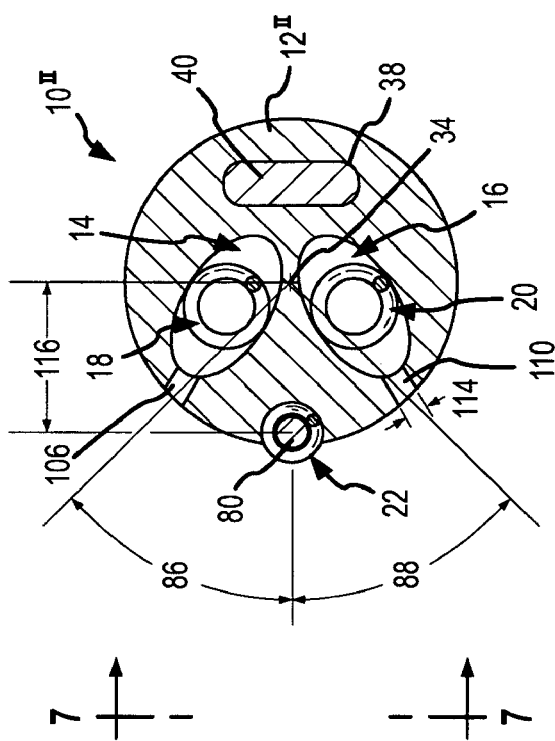
FIG. 6 is a cross-sectional view of a multipolar, multi-lumen, virtual-electrode catheter according to a second embodiment of the present invention.
Figure 7:
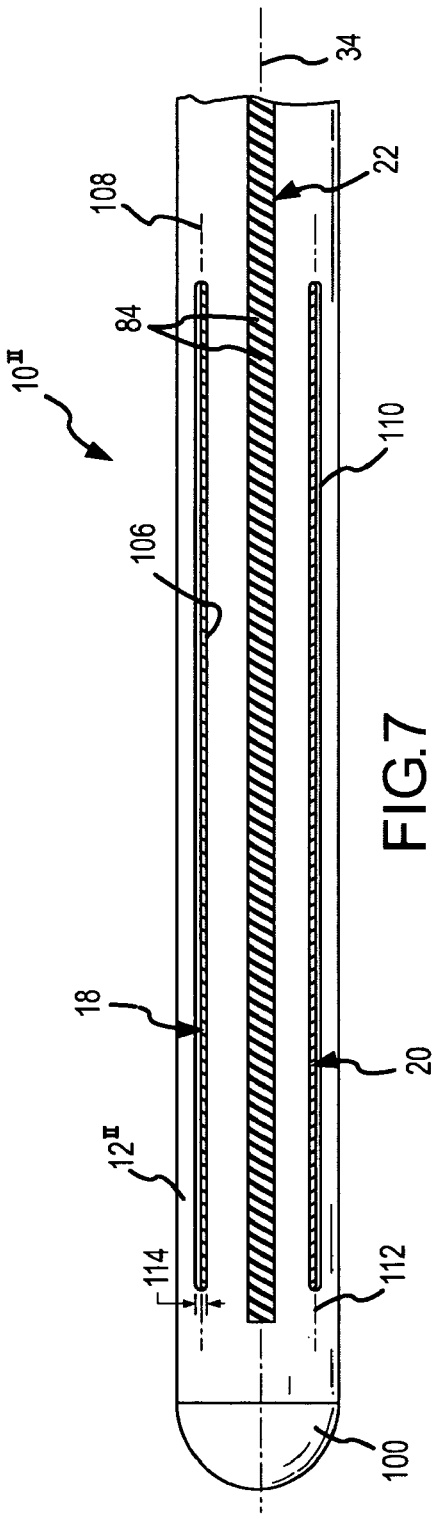
FIG. 7 is similar to FIG. 5, but is a front elevation of the multipolar, multi-lumen, virtual-electrode catheter according to the second embodiment, taken in the direction of line 7-7 of FIG. 6.

FIGS. 6 and 7 depict views of a distal portion 10$^{II}$, of a multipolar, multi-lumen virtual-electrode catheter according to a second embodiment of the present invention. This second embodiment is similar to the first embodiment. The exit feature, however, comprises a first exit slot 106 that extends longitudinally along a first longitudinally-extending slot centerline 108 and through an external wall of the catheter body 12$^{II}$ and into the first elliptical internal lumen 14; and a second exit slot 110 that extends longitudinally along a second longitudinally-extending slot centerline 112 and through an external wall of the catheter body 12$^{II}$ and into the second elliptical internal lumen 16. The two slots 106, 110 replace the two rows of exit portholes 26, 30 of the first embodiment. The slot width 114 of each slot may be, for example, 0.007 inches (i.e., approximately 0.18 mm). In this second embodiment, a single large internal coil 18, 20 is again present in each internal lumen 14, 16, and the surface electrode 22 is again depicted as a single coil partially embedded in an exterior sidewall of the catheter main body 12$^{II}$. In the depicted embodiment, the surface electrode 22 is inset into the outer surface of the catheter main body 12$^{II}$ such that the surface electrode longitudinal axis 90 (see FIG. 1) is offset a distance 116 of approximately 0.041 inches (i.e., approximately 1.04 mm) in front of the catheter longitudinal axis 34.

It is possible that, if the anchored distal projection 104 were not present, the large internal coils 18, 20 may not extend over the first and second pluralities of exit portholes 26, 30 respectively, (first embodiment) or over the entire length of the exit slots 106, 110 (second embodiment). If the large internal coils 18, 20 were not present over one or more of the exit portholes 26, 30, for example, the saline or other conductive fluid 36 being flushed around, along, and within the large internal coils 18, 20 may get too hot during use. In particular, as the conductive fluid moves around, along, and within the large internal coils, energy traveling through that coils is delivered to the conductive fluid for ultimate delivery through the exit portholes (or slots) to the dispersive electrode (i.e., the surface electrode 22 visible in FIGS. 1-3, 5, 6, and 7). This energy delivery causes heating of the conductive fluid, which, in addition to carrying energy, also serves a cooling function. If the large internal coils 18, 20 do not extend over a couple of portholes 26, 30, for instance, a disproportionately high percentage of the cooling fluid 36 may exit from those "uncovered" and thus unrestricted portholes. This would potentially starve the remaining portholes of cooling fluid, resulting in potential heat build-up at these "covered" and thus restricted portholes, possibly leading to increased coagulum formation at the portholes experiencing reduced flow.

Similarly, if the large internal coils 18, 20 were to shift proximally and thus no longer extend over the distal portion of one or both of the slots 106, 110, for example, the flow of the saline or other conductive fluid 36 through this portion of the slots may increase, thereby "starving" the remainder of the slots of cooling fluid, leading to possible increases in coagulum formation along the portion or portions of the slot or slots experiencing reduced flow of cooling fluid. By anchoring the distal end of each of the large internal coils to the terminal sphere 100, these unexpected and undesirable variations in the volume of fluid flowing through different portions of the slots or through different exit portholes can be better controlled. If the most distal portholes or the most distal portion of one or both of the slots were to become blocked, it would become increasingly difficult to get uniform flow from the remaining portholes or the remaining portion of the slots since the saline flowing in the elliptical internal lumens 18, 20 may then be flowing at a rate that is no longer correctly tailored to the total area of the "exit opportunities."

Figure 8:
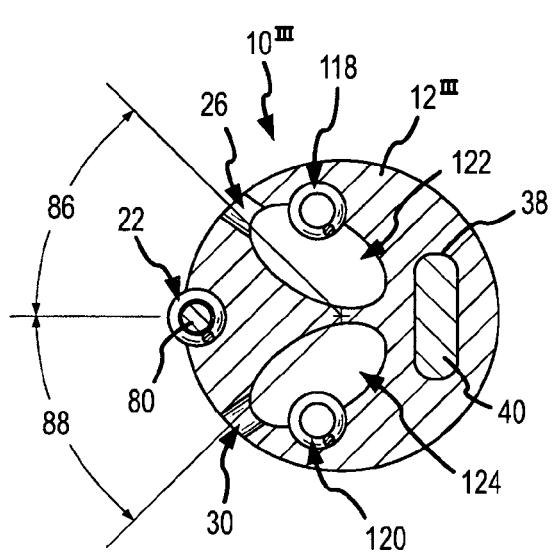
FIG. 8 is a cross-sectional view of a multipolar, multi-lumen, virtual-electrode catheter according to a third embodiment of the present invention.

FIG. 8 is similar to FIGS. 2 and 6, but depicts a cross-sectional view of a distal portion 10$^{III}$ of a multipolar, multi-lumen virtual-electrode catheter according to a third embodiment of the present invention. The third embodiment is most similar to the first embodiment. In the third embodiment, however, the single large internal coil electrode 18, 20 in each internal lumen 14, 16 has been replaced by a single small internal coil electrode 118, 120. In other words, in the embodiment depicted in FIG. 8, the internal flexible current carrier or electrode in each internal lumen is a single small coil electrode 118, 120 that is partially embedded in a sidewall of the internal lumen 122, 124, respectively. These single small internal electrodes 118, 120 accommodate, for example, a higher flow volume of conductive fluid through the elliptical internal lumens 122, 124, respectively, since the internal lumens have less of their cross-sectional area obscured or blocked by the internal flexible electrodes. The catheter body 12$^{III}$ depicted in FIG. 8 again includes the optional wire or rail 40 for shaping or steering the distal portion 10$^{III}$ of the virtual-electrode catheter. This third lumen 38 and the wire or rail 40 need not be present (compare, e.g., FIG. 13).

Figure 9:
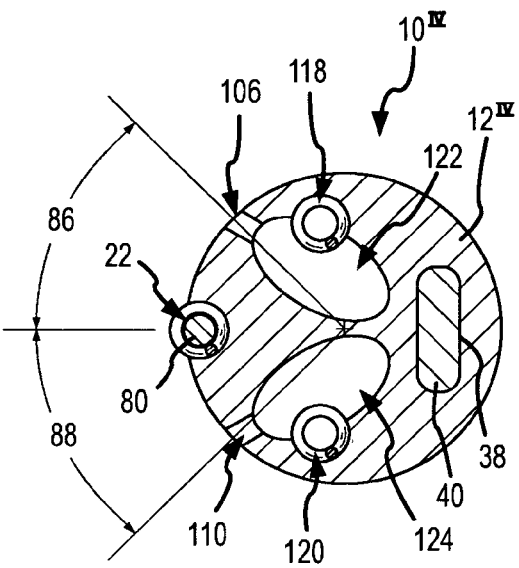
FIG. 9 is similar to FIG. 8, but is a cross-sectional view of a multipolar, multi-lumen, virtual-electrode catheter according to a fourth embodiment of the present invention.

FIG. 9 is a cross-sectional view similar to FIGS. 2, 6, and 8, but depicts a distal portion 10$^{IV}$ of a fourth embodiment of the present invention. The fourth embodiment is most similar to the second embodiment, but the large internal coil 18, 20 in each of the internal lumens has again been replaced by a small internal coil 118, 120. This fourth embodiment comprises a first exit slot 106 and a second exit slot 110 like the exit slots depicted in the embodiment of FIGS. 6 and 7. FIG. 9 again shows the surface electrode coil 22 partially embedded in the exterior surface of the catheter body 12$^{IV}$.

Figure 10:
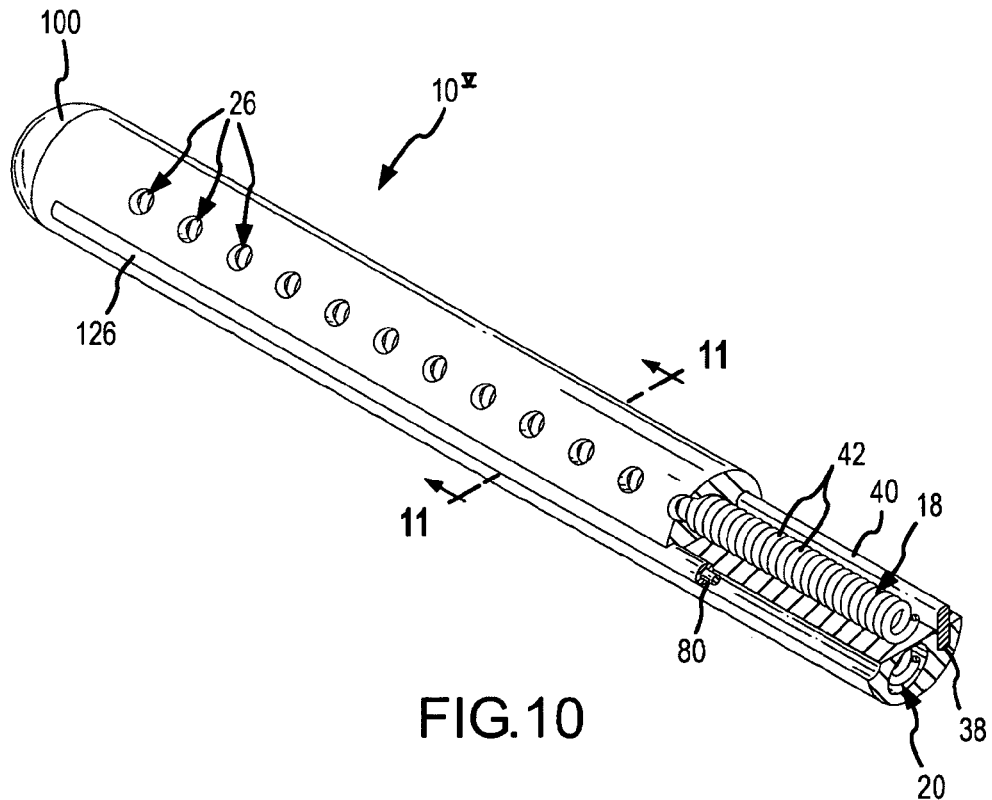
FIG. 10 is similar to FIG. 1, but depicts a fragmentary, isometric view of a multipolar, multi-lumen, virtual-electrode catheter according to a fifth embodiment of the present invention, with a portion of the catheter body broken-away to reveal various internal features.
Figure 11:
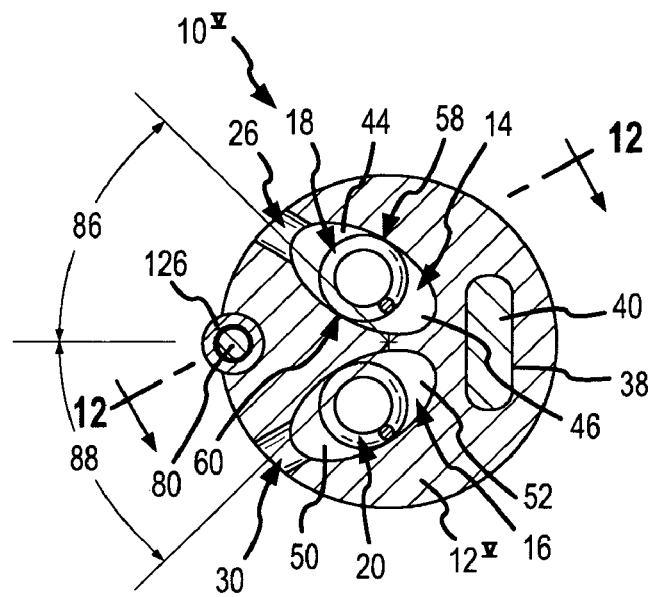
FIG. 11 is a cross-sectional view of the multipolar, multi-lumen, virtual-electrode catheter according to the fifth embodiment of the present invention, taken along line 11-11 of FIG. 10.
Figure 12:
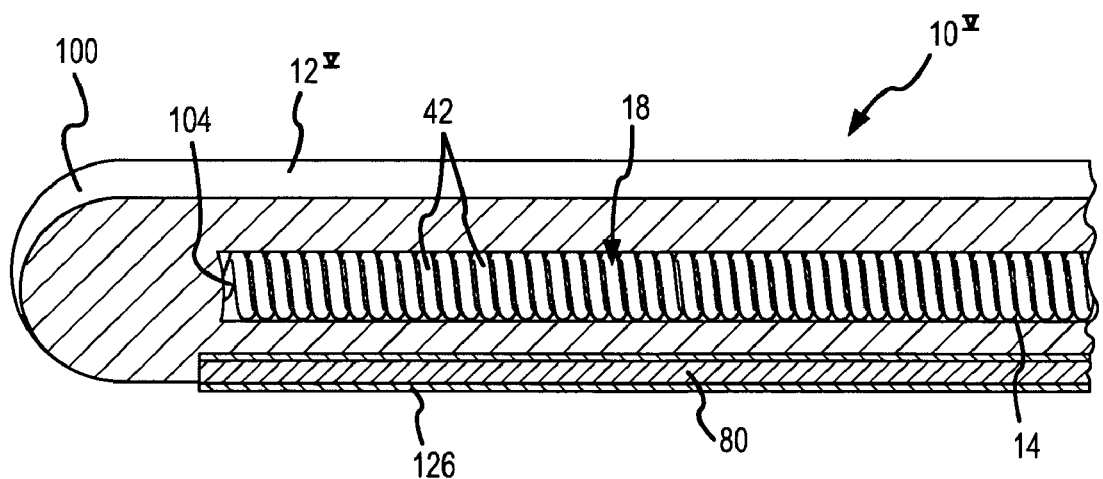
FIG. 12 is a fragmentary, cross-sectional view of the multipolar, multi-lumen, virtual-electrode catheter according to the fifth embodiment of the present invention, taken along line 12-12 of FIG. 11.

FIGS. 10-12 depict a distal portion 10$^V$ of a multipolar, multi-lumen virtual-electrode catheter according to a fifth embodiment of the present invention. FIG. 11 is similar to FIG. 10. In the fifth embodiment, however, the surface electrode 126 is a thermally and electrically conductive tube rather than a coil (FIG. 1). This surface electrode tube 126 may be metal, or may be constructed from some other conductive material (e.g., conductive silicone carbide or conductive polymer). For example, the surface electrode tube depicted in FIGS. 10-12 may be a NiTi metal tube, potentially having shape memory characteristics. The surface electrode tube may, accordingly, provide some force that helps shape the distal portion 10$^V$ of the multipolar, multi-lumen virtual-electrode catheter as the catheter is placed adjacent to the tissue 62 to be treated.

In the fifth embodiment, a thermal sensor 80 is inserted into the center or core of the surface electrode tube 126. Since the surface electrode tube in this embodiment is not cooled, being able to monitor the temperature of the surface electrode tube 126 via the thermal sensor 80 allows the user an opportunity to prevent overheating of this electrode tube during use. In the embodiments depicted in FIGS. 1-9, each of which comprises a surface electrode coil 22, blood may become caught or trapped in the gaps 82 between the individual turns 84 of the surface electrode coil 22. Thus, it is possible that this blood 76 in the gaps between adjacent coils of the surface electrode coil may become excessively heated during use of the virtual-electrode catheter to the point of forming coagulum. The surface electrode tube 126 of the fifth embodiment may alleviate some of these potential coagulation issues that may be present with a surface electrode coil 22.

FIG. 11 is a cross-sectional view taken along 11-11 of FIG. 10. This figure again shows the surface electrode tube 126 partially embedded in the exterior surface of the catheter body $12^V$. As shown in FIGS. 10-12, the surface electrode tube is completely filled by the thermal sensor 80. In an alternative form, however, the thermal sensor may not completely fill the internal volume of the surface electrode tube, or the thermal sensor may be completely absent from the inside of the electrode tube. In either of these latter alternative configurations, a cooling fluid may be present inside of (possibly flowing within) the surface electrode tube. For example, the surface electrode tube may carry room temperature saline to provide some cooling and heat dissipation as the surface electrode tube performs its function of a dispersive electrode and receives energy from the internal flexible electrodes 18, 20 (e.g., the large internal coils depicted in FIGS. 10-12).

FIG. 12 is a fragmentary, cross-sectional view taken along line 12-12 of FIG. 11. As shown in this figure, the outer diameter 56 (see FIG. 2) of each of the large internal coils 18, 20 may be selected in order to substantially, if not completely, bridge the distance between the top 58 and bottom 60 of the elliptical internal lumen 14, 16 in which the internal coil 18, 20, respectively, is mounted. In other words, the outer diameter 56 of each large internal coil 18, 20 may be substantially the same as the length 57 (see FIG. 2) of the minor axis of the elliptical cross section of the internal lumen 14, 16 in which the coil is mounted. Since line 12-12 of FIG. 11 slices through the distal portion $10^V$ of the virtual-electrode catheter adjacent to the points where the outer surface of the large internal coil 18 contacts the inner surface of the elliptical internal lumen 14, the large internal coil 18 is depicted in FIG. 12 as substantially filling the elliptical internal lumen 14. The forward (44, 50) and rearward (46, 52) crescent-moon-shaped flow channels would, however, remain present in the configuration depicted in FIGS. 10-12.

Figure 13:
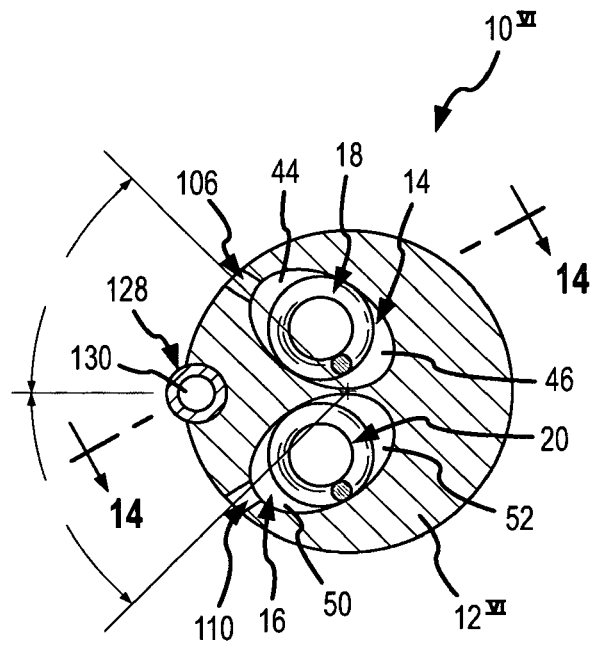
FIG. 13 is a cross-sectional view of a multipolar, multi-lumen, virtual-electrode catheter according to a sixth embodiment of the present invention.
Figure 14:
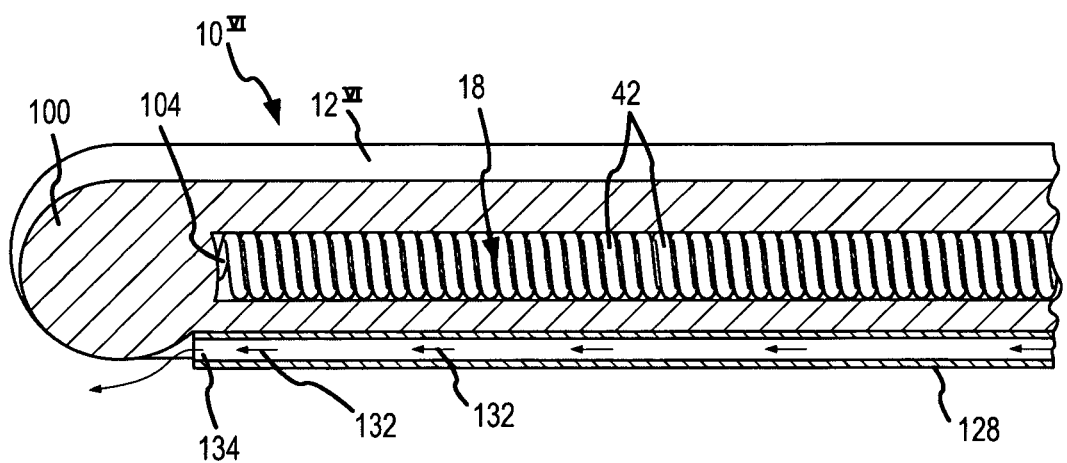
FIG. 14 is a fragmentary, cross-sectional view of the multipolar, multi-lumen, virtual-electrode catheter according to the sixth embodiment of the present invention, taken along line 14-14 of FIG. 13.

FIGS. 13 and 14 depict a distal portion $10^{VI}$ of a sixth embodiment of the multipolar, multi-lumen virtual-electrode catheter according to the present invention. This embodiment is similar to the first embodiment (FIGS. 1-5) and the fifth embodiment (FIGS. 10 and 11). In this embodiment, however, the tubular surface electrode 128, which is shown as being partially embedded in the exterior surface of the catheter body $12^{VI}$, is specifically configured to accommodate flow of a cooling fluid through it. As is clearly visible from each of FIGS. 13 and 14, the flow-through, tubular surface electrode has a hollow core 130 and is thus able to accommodate the flow of a cooling fluid 132. As shown in FIG. 14, the surface electrode tube 128 includes an open distal end or exit port 134. Thus, the fluid 132 flowing through the surface electrode tube 128 can continue to flow and will not become stagnant. Since the surface electrode tube 128 is less likely to get hot in this embodiment that includes cooling fluid 132, no thermal sensors are depicted in FIGS. 13 and 14. However, thermal sensors may be juxtaposed adjacent to the surface electrode tube if it remains desirable or preferable to monitor the temperature of the surface electrode tube during use of the multipolar, multi-lumen virtual-electrode catheter according to this embodiment.

As suggested by FIG. 14, which is a cross-sectional view of the distal portion $10^{VI}$ of a multipolar, multi-lumen virtual-electrode catheter according to the sixth embodiment, taken along line 14-14 of FIG. 13, this embodiment may use two fluid sources (not shown). For example, a first fluid source may supply cooling fluid 132 to the surface electrode tube 128, and a second fluid source may provide conductive fluid 36 (see e.g., FIG. 4) to the elliptical internal lumens 14, 16 in which the large internal coils 18, 20 depicted in FIGS. 13 and 14 reside. The exit port 134 shown in FIG. 14 may be somewhat constricted to control the rate of flow through the surface electrode tube 120. Since it is possible that the ablative energy (e.g., RF energy) being delivered to the conductive fluid 36 that ultimately departs the exit slots 106, 110 may reach the fluid 132 flowing through the exit port 134 of the surface electrode tube 128, having two separate fluid supply systems is desirable. In order to control the total amount of saline delivered into the patient's bloodstream 76 (FIGS. 22-27), however, it is desirable to balance the fluid 36 exiting through the exit slots 106, 110 with the fluid 132 exiting through the surface electrode tube 128. For example, it may be desirable to restrict the total fluid entering the patient's bloodstream to 3-18 ml per minute for certain wattages or amounts of RF energy delivered.

With separate fluid sources, it also is possible to avoid an unintended short circuit. The fluid 132 flowing through the surface electrode tube 128 is not being used as part of a virtual-electrode in this particular embodiment. This fluid 132 is being used for cooling only. Thus, the surface electrode tube 128 acts as a "normal" electrode rather than a virtual electrode. Alternatively, a closed system may be used to deliver cooling fluid to the surface electrode tube. In this closed system, cooling fluid may be delivered to the surface electrode tube from the first fluid source, and then the same fluid may be returned to the first fluid source via a return tube or pathway (not shown). In contrast, an open system is used to deliver saline or other conductive fluid out of the exit slots 106, 110, which are acting as part of a virtual electrode with cooling effects. It should be noted, as alluded to above, the sixth embodiment, as depicted in FIGS. 13 and 14, does not include a rail lumen 38 or rail 40 (e.g., FIG. 2).

Although the fifth embodiment (FIGS. 11 and 12) and the sixth embodiment (FIGS. 13 and 14) of the present invention each show only one surface electrode tube 126, 128, respectively, being used, the present invention contemplates the use of multiple surface electrode tubes, similar to the surface electrode coils that are described next in connection with, for example, FIGS. 15-21.

FIGS. 15-17 depict three views of a distal portion $10^{VII}$ of a multipolar, virtual-electrode catheter according to a seventh embodiment of the present invention. This embodiment is similar to the embodiment depicted in FIGS. 1-5. In the seventh embodiment, however, a first outboard surface electrode 136, a second outboard surface electrode 138, and an intermediate surface electrode 140 are present and, as depicted in FIGS. 15-17, are each partially embedded into the outer surface of the catheter body $12^{VII}$. The first outboard surface electrode 136, the second outboard surface electrode 138, and the intermediate surface electrode 140 are small, longitudinally-extending coils that straddle the porthole centerlines 28, 32. In particular, as shown in FIG. 17, the first outboard surface electrode 136 and the intermediate surface electrode 140 straddle the first longitudinally-extending porthole centerline 28, and the second outboard surface electrode 138 and the intermediate surface electrode 140 straddle the second longitudinally-extending porthole centerline 32. As will be described further below in connection with FIGS. 25-27, this particular configuration provides additional options for the user of this virtual-electrode catheter.

Similar to what was previously discussed in connection with FIG. 2, the radial offset angles 142, 144, 146, 148, depicted in FIG. 16, which include a first inboard radial offset angle 142, a second inboard radial offset angle 144, a first outboard radial offset angle 146, and a second outboard radial offset angle 148, are selected to facilitate desired, effective creation of one or more electric fields 174, 176, 178, 182 (see, e.g., FIGS. 25-27) in the tissue 62 being ablated (see FIGS. 25-27). The first and second inboard radial offset angles 142, 144, respectively, may be, for example, 45°. Further, in one example, wherein the multipolar, multi-lumen virtual-electrode catheter has the circular cross section depicted in FIGS. 15-17, and the diameter 24 (FIG. 17) of that circular cross section is approximately 0.091 (i.e., approximately 2.31 mm), the center of the intermediate surface electrode coil 140, which lies in a plane of symmetry 150 of this embodiment of the catheter, may be offset forward of the center of the catheter body by a distance 152 of approximately 0.041 inches (i.e., approximately 1.04 mm), the respective centers of the first and second outboard surface electrode coils 136, 138 may be offset rearward of the center of the catheter body by a distance 154 of approximately 0.007 inches (i.e., approximately 0.18 mm), the center of the first outboard surface electrode coil 136 may be displaced a distance 156 of approximately 0.040 inches (i.e., approximately 1.02 mm) above the catheter's plane of symmetry 150, and the center of the second outboard surface electrode coil 138 may be displaced a distance 158 of approximately 0.040 inches (i.e., approximately 1.02 mm) below the catheter's plane of symmetry 150.

Figure 18:
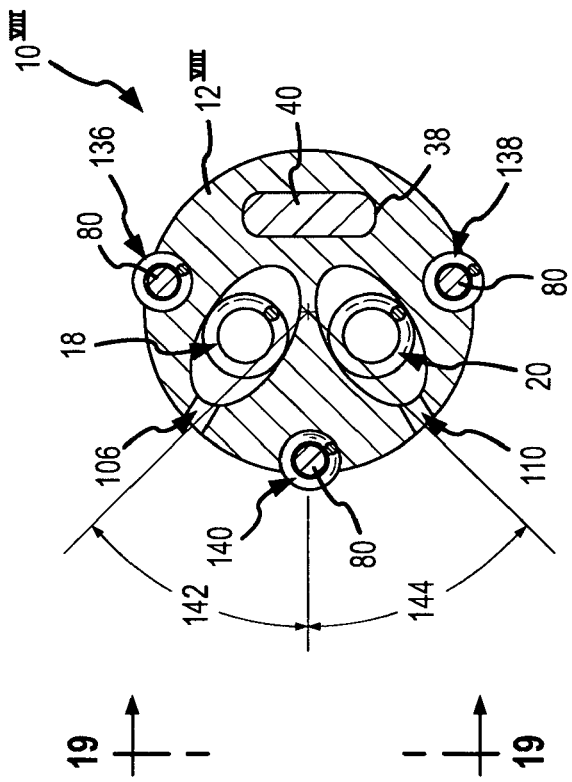
FIG. 18 is a cross-sectional view of a multipolar, multi-lumen, virtual-electrode catheter according to an eighth embodiment of the present invention.
Figure 19:
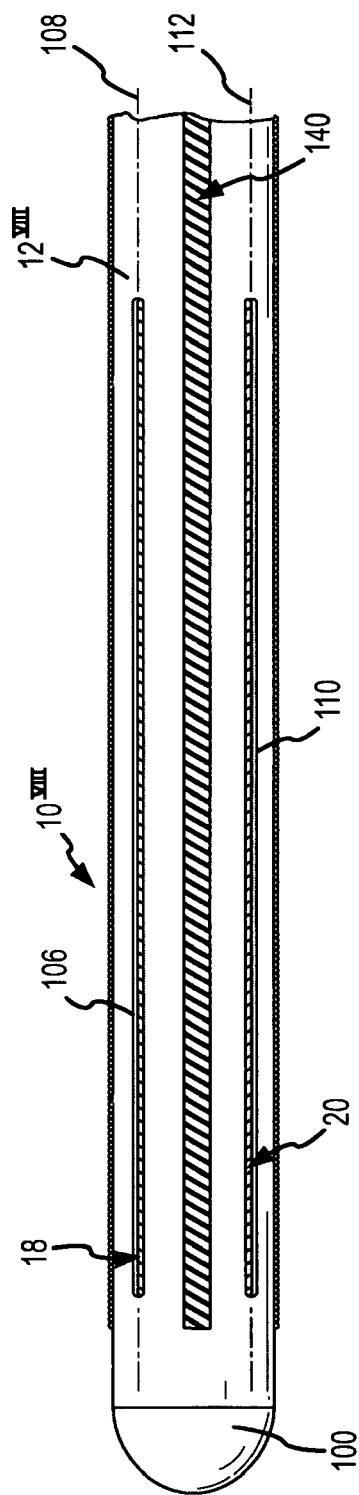
FIG. 19 is a front elevation of the embodiment depicted in FIG. 18 taken in the direction of line 19-19 of FIG. 18.

FIGS. 18 and 19 are similar to FIGS. 16 and 17, respectively, but depict a distal portion $10^{VIII}$ of a multipolar, virtual-electrode catheter according to an eighth embodiment of the present invention. In this eighth embodiment, the first plurality of exit portholes 26 has been replaced by a first exit slot 106, and the second plurality of exit portholes 30 has been replaced by a second exit slot 110. These first and second exit slots 106, 110 may be, for example, 0.007 inches wide (i.e., approximately 0.18 mm wide) (see, e.g., FIG. 7). The surface electrodes 136, 138, 140 are again shown as being partially embedded in the outer surface of the catheter body $12^{VIII}$. Similarly, in all other aspects, the eighth embodiment is like the previously-discussed embodiments.

Figure 20:
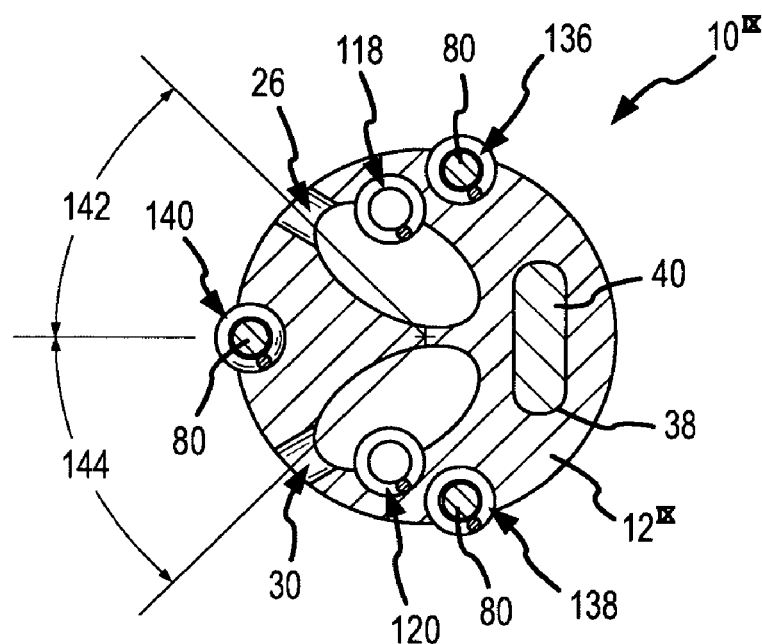
FIG. 20 is a cross-sectional view of a multipolar, multi-lumen, virtual-electrode catheter according to a ninth embodiment of the present invention.

FIG. 20 is a cross-sectional view of a distal portion $10^{IX}$ of a multipolar, virtual-electrode catheter according to a ninth embodiment of the present invention. The ninth embodiment is similar to the seventh embodiment (see FIGS. 15-17). For example, the surface electrodes 136, 138, 140, are again depicted as being partially embedded in the outer surface of the catheter body $12^{IX}$. In the ninth embodiment, however, the large internal coil electrodes 18, 20 have been replaced by small internal coil electrodes 118, 120, similar to the small internal coil electrodes 118, 120 depicted in FIGS. 8 and 9, and discussed further above.

Figure 21:
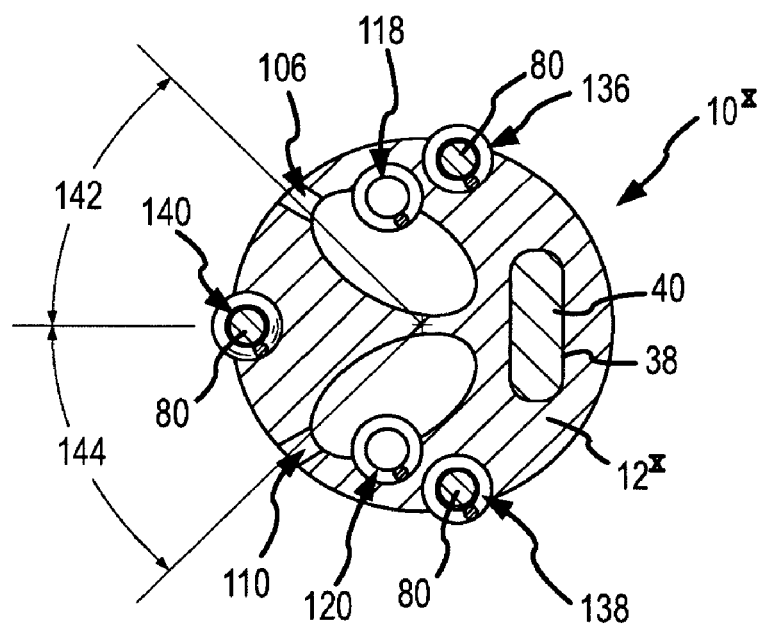
FIG. 21 is a cross-sectional view of a multipolar, multi-lumen, virtual-electrode catheter according to a tenth embodiment of the present invention.

FIG. 21 is a cross-sectional view of a distal portion $10^{X}$ of a multipolar, virtual-electrode catheter according to a tenth embodiment of the present invention. The tenth embodiment of the virtual-electrode catheter is similar to the eighth embodiment (see FIGS. 18 and 19). Thus, the surface electrodes 136, 138, 140 are again depicted as being partially embedded in the outer surface of the catheter body $12^{X}$. The large internal coil electrodes 18, 20, however, have been replaced with the small internal coil electrodes 118, 120. The small internal coil electrodes 118, 120 depicted in FIG. 21 are similar to the small internal coil electrodes previously discussed in connection with FIGS. 8 and 9.

As mentioned, the surface electrode tubes 126, 128 depicted in, for example, FIGS. 10 and 14, respectively, may be used in place of the surface electrode coils 136, 138, 140 depicted in FIGS. 17-21.

Figure 22:
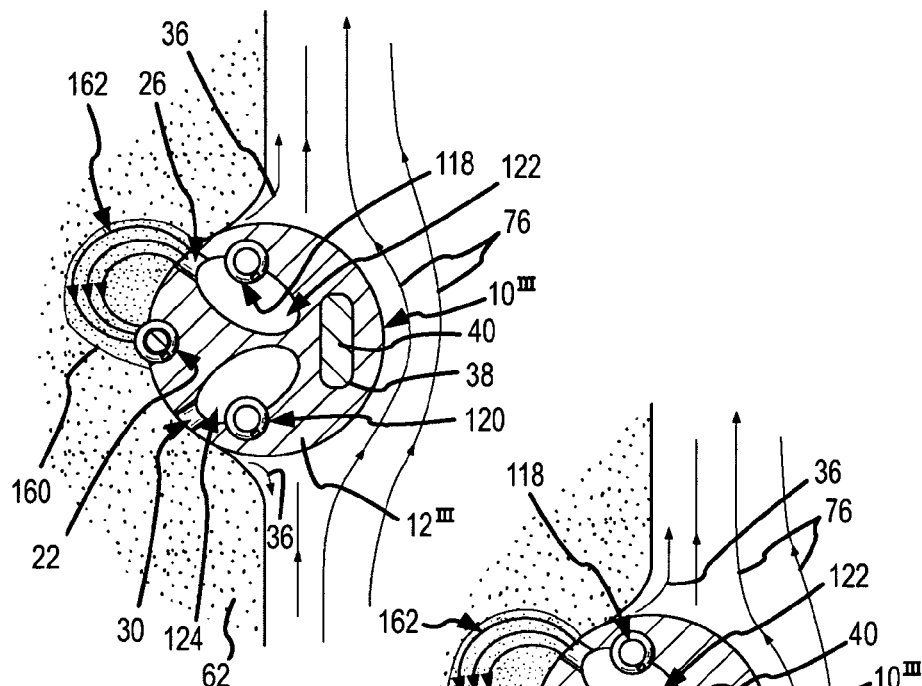
FIG. 22 is a cross-sectional view of the multipolar, multi-lumen, virtual-electrode catheter depicted in FIG. 8 being used in a first operating mode to treat tissue.

FIG. 22 is a cross-sectional view of the distal portion $10^{III}$ of the multipolar, multi-lumen, virtual-electrode catheter depicted in FIG. 8 being used in a first operating mode to treat tissue. In particular, FIG. 22 is a cross-sectional view of the distal portion $10^{III}$ of the multipolar, multi-lumen virtual-electrode catheter according to the third embodiment of the present invention being pressed against tissue 62 to form a lesion 160. The portion of the catheter that is not against the tissue 62 is surrounded by blood that is represented schematically in FIG. 22 by the lines 76. As shown in FIG. 22, in this first mode, the first, small internal coil electrode 118 acts as the active electrode, creating a first electric field 162 that extends between the first plurality of exit portholes 26 and the surface electrode 22. This first electric field 162 passes through the tissue 62 to create the desired lesion 160. In particular, during operation, conductive fluid 36 (see also, e.g., FIG. 4) flowing through the first elliptical internal lumen 122 is in contact with the active first, small, internal coil electrode 118. This internal coil electrode 118, together with the conductive fluid 36, thus acts as a virtual electrode with the conductive fluid 36 carrying the ablative energy (e.g., the RF energy) to the tissue 62 via the first electric field 162 that is established between the active electrode (i.e., the first, small internal coil electrode 118) and the passive electrode (i.e., the surface electrode 22).

Figure 23:
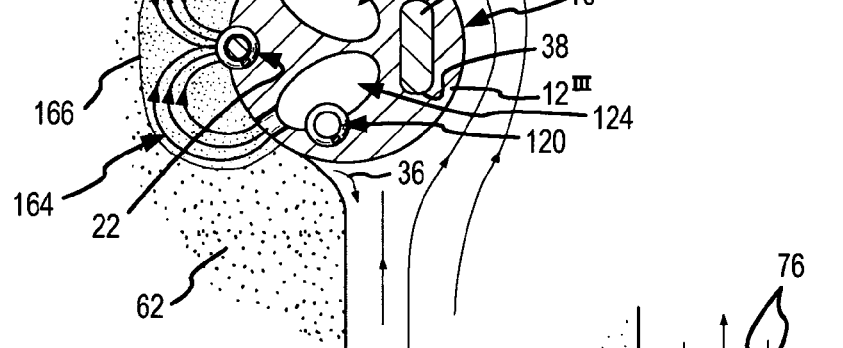
FIG. 23 is a cross-sectional view of the multipolar, multi-lumen, virtual-electrode catheter depicted in FIG. 8 being used in a second operating mode to treat tissue.

FIG. 23 is similar to FIG. 22, but is a cross-sectional view of the distal portion $10^{III}$ of the multipolar, virtual-electrode catheter according to the third embodiment of the present invention (see FIG. 8) in contact with the tissue 62 to be ablated and operating in a second mode. In this second mode, both small, internal coil electrodes 118, 120 are active. Thus, the first electric field 162 is established between the first, small internal coil electrode 118 and the passive electrode (i.e., the surface electrode 22); and a second electric field 164 is established between the second, small internal coil electrode 120 and the passive electrode 22. In this second mode, the virtual-electrode catheter would create a lesion 166 that is larger than the lesion 160 being created in FIG. 22.

Figure 24:
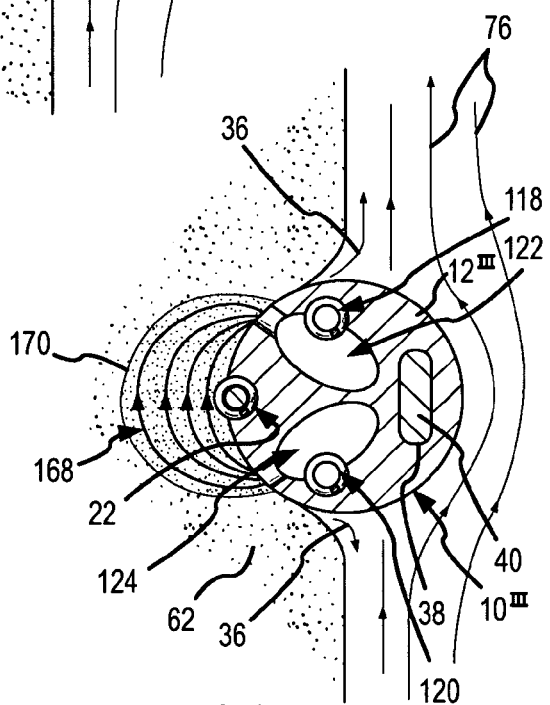
FIG. 24 is a cross-sectional view of the multipolar, multi-lumen, virtual-electrode catheter depicted in FIG. 8 being used in a third operating mode to treat tissue.

FIG. 24 also depicts a cross-sectional view of the distal portion $10^{III}$ the multipolar, virtual-electrode catheter of FIG. 8. In FIG. 24, however, the multipolar, multi-lumen, virtual-electrode catheter of FIG. 8 is operating in a third mode. In this third mode, an extended electric field 168 is established between the first and second, small internal coil electrodes 118, 120, respectively, and the surface electrode 22 is not involved. Thus, the lesion being formed is potentially a larger lesion than may be formed in the first operating mode of this virtual-electrode catheter (see FIG. 22), and the lesion being formed is potentially similar in size to the lesion 170 that may be formed in the third operating mode of this virtual-electrode catheter (see FIG. 23). Other operating modes are available for the multipolar, multi-lumen, virtual-electrode catheter depicted in FIG. 8 and FIGS. 22-24.

Figure 25:
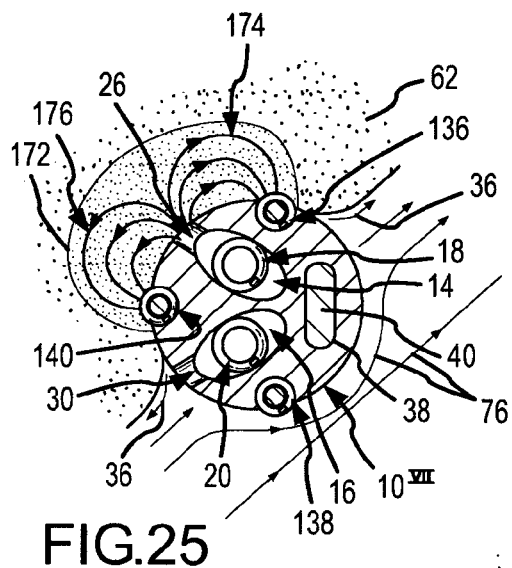
FIG. 25 is a cross-sectional view of the multipolar, multi-lumen, virtual-electrode catheter depicted in FIGS. 15-17 being used in a first operating mode to treat tissue.

FIG. 25 is a cross-sectional view of the distal portion $10^{VII}$ of the multipolar, multi-lumen, virtual-electrode catheter depicted in FIGS. 15-17 being used in a first operating mode to treat tissue 62. In particular, FIG. 25 is a cross-sectional view of the distal portion $10^{VII}$ of the multipolar, multi-lumen virtual-electrode catheter according to the seventh embodiment of the present invention being pressed against tissue 62 to form a lesion 172. The portion of the catheter that is not against the tissue is again depicted as being surrounded by blood that is represented schematically in FIG. 25 by the lines 76. As shown in FIG. 25, in this first mode, the first, large, internal coil electrode 18 acts as the active electrode, creating a first electric field 174 that extends between the first plurality of exit portholes 26 and the first outboard surface electrode 136, and creating a second electric field 176 that extends between the first plurality of exit portholes 26 and the intermediate surface electrode 140. These two electric fields 174, 176 may be created simultaneously or alternatingly. The first and second electric fields pass through the tissue to create the desired lesion 172. In particular, during operation, conductive fluid 36 (see also, e.g., FIG. 4) flowing through the first elliptical internal lumen 14 is in contact with the active first, large, internal coil electrode 18. This internal coil electrode 18, together with the conductive fluid 36, thus acts as a virtual electrode with the conductive fluid carrying the ablative energy (e.g., the RF energy) to the tissue 62 via the first and second electric fields 174, 176 that are established between the active electrode (i.e., the first, large, internal coil electrode 18) and two of the passive surface electrodes 136, 140.

Figure 26:
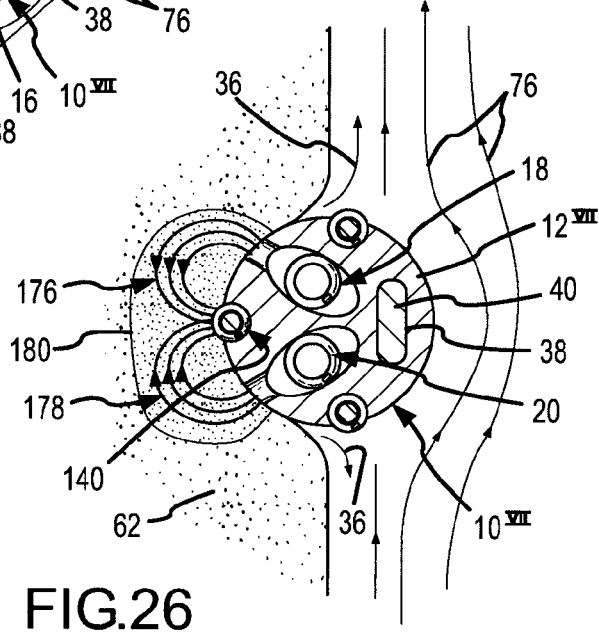
FIG. 26 is a cross-sectional view of the multipolar, multi-lumen, virtual-electrode catheter depicted in FIGS. 15-17 being used in a second operating mode to treat tissue.

FIG. 26 is similar to FIG. 25, but is a cross-sectional view of the distal portion $10^{VII}$ of the multipolar, virtual-electrode catheter according to the seventh embodiment of the present invention (see FIGS. 15-17) in contact with the tissue 62 to be ablated and operating in a second mode. In this second mode, both large, internal coil electrodes 18, 20 are active. Further, the second electric field 176 is established between the first, large, internal coil electrode 18 and the intermediate surface electrode 140; and a third electric field 178 is established between the second, large, internal coil electrode 20 and the intermediate electrode 140. In this second mode, the virtual-electrode catheter would create a lesion 180 that is of a similar size to the lesion 172 being created in FIG. 25, but the location of the lesion 180 has been "rotated" to a different position on the exterior surface of the catheter body $12^{VII}$. Also, the lesion 180 in FIG. 26 is being formed via energy from both internal coil electrodes 18, 20.

Figure 27:
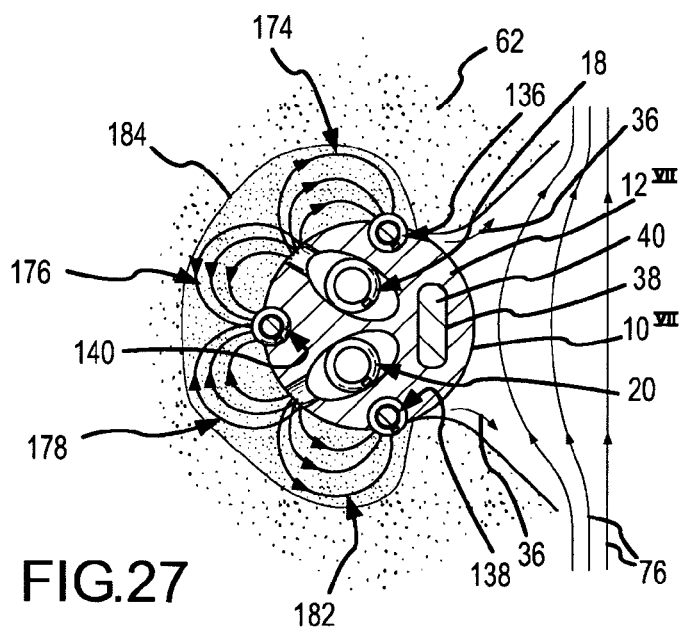
FIG. 27 is a cross-sectional view of the multipolar, multi-lumen, virtual-electrode catheter depicted in FIGS. 15-17 being used in a third operating mode to treat tissue.

FIG. 27 is a cross-sectional view of the distal portion $10^{VII}$ of the multipolar, multi-lumen, virtual-electrode catheter depicted in FIGS. 15-17 being used in a third operating mode to treat tissue 62. In this third mode, four electric fields 174, 176, 178, 182 are established in the tissue. In particular, the first electric field 174 is established between the first, large, internal coil electrode 18 and the first outboard surface electrode 136; the second electric field 176 is established between the first, large, internal coil electrode 18 and the intermediate surface electrode 140; the third electric field is established between the second, large, internal coil electrode 20 and the intermediate surface electrode 140; and a fourth electric field 182 is established between the second, large, internal coil electrode 20 and the second outboard surface electrode 138. Thus, the lesion 184 formed is potentially larger than the lesion that may be formed in the first operating mode of this virtual-electrode catheter (see FIG. 25), and the lesion 184 being formed is also potentially larger than the lesion that may be formed in the second operating mode of this virtual-electrode catheter (see FIG. 26). Other operating modes are available for the multipolar, multi-lumen, virtual-electrode catheter depicted in FIGS. 15-17.

Although ten embodiments of this invention have been described above with a certain degree of particularly, those skilled in the art could make numerous alterations to the disclosed embodiments without departing from the spirit or scope of this invention. For example, as mentioned above, the surface electrode tube 126 depicted in FIGS. 10-12, or the surface electrode tube 128 depicted in FIGS. 13 and 14, could be used in place of the surface electrode coils 22, 136, 138, 140 depicted in the other figures. Also, although portholes 26, 30 with circular cross sections and longitudinally-extending slots 106, 110 are depicted in the figures for all of the embodiments described above, the "exit opportunities" may comprise other shapes and sizes, for example, micro-pores or holes with other than circular cross sections may be used. If properly configured, for example, micro-pores may be used to establish the desired flow characteristics for the conductive fluid as it exits the distal portion of the virtual-electrode catheter. Further, although the catheter body is depicted in all of the figures with a circular cross section, the catheter body need not have a circular cross section. Also, the virtual-electrode catheter may comprise additional surface electrodes and may comprise more than two internal fluid lumens. Among the advantages of the instant invention over the prior art are (i) improved efficiency of RF ablation; (ii) improved efficiency of RF ablation using virtual-electrode technology; (iii) the ability to localize RF energy delivery to tissue; (iv) the ability to form lesions using low RF power; and (v) the ability to form lesions while introducing a small volume of fluid into a patient during lesion formation. Using the embodiments described above, for example, lesions may be obtained at low powers (e.g., 10 to 30 watts) and low fluid flow rates (e.g., 3 to 6 ml per minute through the internal fluid lumens). All directional references (e.g., upper, lower, upward, downward, left, right, leftward, rightward, forward, rearward, top, bottom, above, below, vertical, horizontal, clockwise, and counterclockwise) are only used for identification purposes to aide the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit or scope of the invention as defined in the appended claims.

What is claimed is:

1. A multipolar, multi-lumen, virtual-electrode catheter for treatment of tissue, the catheter comprising
   (a) a catheter body having
      an outer surface;
      a first sidewall;
      a second sidewall;
      a first longitudinally-extending internal lumen, extending adjacent to said first sidewall and adapted to transport conductive fluid; and
      a second longitudinally-extending internal lumen, extending adjacent to said second sidewall and adapted to transport conductive fluid;
   (b) a first exit feature extending through said first sidewall of said catheter body, wherein said first exit feature thereby fluidly couples said first internal lumen to said outer surface of said catheter body;
   (c) a second exit feature extending through said second sidewall of said catheter body, wherein said second exit feature thereby fluidly couples said second internal lumen to said outer surface of said catheter body;
   (d) a first internal electrode residing within at least a distal portion of said first internal lumen and adapted to deliver treatment energy to the tissue via said conductive fluid and said first exit feature;
   (e) a second internal electrode residing within at least a distal portion of said second internal lumen and adapted to deliver treatment energy to the tissue via said conductive fluid and said second exit feature; and (f) at least one surface electrode mounted on said outer surface of said catheter body adjacent to said first and second exit features.

2. The multipolar, multi-lumen, virtual-electrode catheter of claim 1, wherein said at least one surface electrode is selected from the group consisting of a conductive coil and a conductive tube.

3. The multipolar, multi-lumen, virtual-electrode catheter of claim 2, wherein said at least one surface electrode is mounted in and retained by a longitudinally-extending, C-shaped channel on said outer surface of said catheter body.

4. The multipolar, multi-lumen, virtual-electrode catheter of claim 2, wherein said at least one surface electrode comprises a thermally and electrically conductive surface electrode tube, and wherein said catheter further comprises a temperature sensor within a core of said at least one surface electrode tube.

5. The multipolar, multi-lumen, virtual-electrode catheter of claim 1, wherein said at least one surface electrode is a cooled electrode.

6. The multipolar, multi-lumen, virtual-electrode catheter of claim 5, wherein said at least one surface electrode comprises a coil of wound, tubular metal adapted to carry a surface-electrode cooling fluid.

7. The multipolar, multi-lumen, virtual-electrode catheter of claim 5, wherein said at least one surface electrode comprises at least one hollow surface electrode tube constructed from a thermally and electrically conductive material and adapted to carry a surface-electrode cooling fluid in a core of said at least one surface electrode tube.

8. The multipolar, multi-lumen, virtual-electrode catheter of claim 7, wherein said first and second internal lumens are adapted to receive conductive fluid from a first fluid source, and wherein said at least one surface electrode tube is adapted to receive said surface-electrode cooling fluid from a second fluid source.

9. The multipolar, multi-lumen, virtual-electrode catheter of claim 7, wherein said at least one surface electrode tube further comprises an open distal end adapted to permit said surface-electrode cooling fluid to exit said at least one surface electrode tube.

10. The multipolar, multi-lumen, virtual-electrode catheter of claim 1, wherein said at least one surface electrode comprises a plurality of surface electrodes on said outer surface of said catheter body, and wherein at least one of said plurality of surface electrodes acts as a dispersive electrode.

11. The multipolar, multi-lumen, virtual-electrode catheter of claim 1, wherein said first exit feature and said second exit feature are each selected from the group consisting of a plurality of exit portholes, at least one exit slot, and a plurality of micro-pores.

12. The multipolar, multi-lumen, virtual-electrode catheter of claim 1, wherein said first exit feature comprises a first longitudinally-extending exit slot that extends longitudinally along a first longitudinally-extending slot centerline and through said first sidewall of said catheter body and into said first longitudinally-extending internal lumen; and wherein said second exit feature comprises a second longitudinally-extending exit slot that extends longitudinally along a second longitudinally-extending slot centerline and through said second sidewall of said catheter body and into said second longitudinally-extending internal lumen.

13. The multipolar, multi-lumen, virtual-electrode catheter of claim 12, wherein said first internal electrode comprises a first internal coil electrode, wherein said first internal coil electrode extends over an entire length of said first exit slot, wherein said second internal electrode comprises a second internal coil electrode, and wherein said second internal coil electrode extends over an entire length of said second exit slot.

14. The multipolar, multi-lumen, virtual-electrode catheter of claim 1, wherein said first exit feature comprises a first plurality of exit portholes extending through said first sidewall of said catheter body; and wherein said second exit feature comprises a second plurality of exit portholes extending through said second sidewall of said catheter body.

15. The multipolar, multi-lumen, virtual-electrode catheter of claim 14, wherein said first plurality of exit portholes extend radially through said first sidewall relative to a catheter longitudinal axis; and wherein said second plurality of exit portholes extend radially through said second sidewall relative to said catheter longitudinal axis.

16. The multipolar, multi-lumen, virtual-electrode catheter of claim 14, wherein said first plurality of exit portholes are arranged along a first longitudinally-extending porthole centerline on said outer surface of said catheter body, and wherein said second plurality of exit portholes are arranged along a second longitudinally-extending porthole centerline on said outer surface of said catheter body.

17. The multipolar, multi-lumen, virtual-electrode catheter of claim 16, wherein a longitudinal axis of said at least one surface electrode is radially offset on said outer surface of said catheter body from said first longitudinally-extending porthole centerline by a first radial offset angle; and wherein said longitudinal axis of said at least one surface electrode is radially offset on said outer surface of said catheter body from said second longitudinally-extending porthole centerline by a second radial offset angle.

18. The multipolar, multi-lumen, virtual-electrode catheter of claim 17, wherein said first radial offset angle is the same as said second radial offset angle.

19. The multipolar, multi-lumen, virtual-electrode catheter of claim 16, wherein said at least one surface electrode comprises a first outboard surface electrode, a second outboard surface electrode, and an intermediate surface electrode mounted on said outer surface of said catheter body.

20. The multipolar, multi-lumen, virtual-electrode catheter of claim 19, wherein said first outboard surface electrode and said intermediate surface electrode straddle said first longitudinally-extending porthole centerline, and wherein said second outboard surface electrode and said intermediate surface electrode straddle said second longitudinally-extending porthole centerline.

21. The multipolar, multi-lumen, virtual-electrode catheter of claim 14, wherein said first internal electrode comprises a first, internal coil electrode, and wherein said first, internal coil electrode extends adjacent to each porthole of said first plurality of exit portholes; and wherein said second internal electrode comprises a second, internal coil electrode, and wherein said second, internal coil electrode extends adjacent to each porthole of said second plurality of exit portholes.

22. The multipolar, multi-lumen, virtual-electrode catheter of claim 21, wherein said first, internal coil electrode has a first annular cross-sectional shape, wherein said second, internal coil electrode has a second annular cross-sectional shape, wherein said first longitudinally-extending internal lumen has a first elliptical cross-sectional shape, wherein said second longitudinally-extending internal lumen has a second elliptical cross-sectional shape, wherein a first flow channel is define by first interstices between said first annular cross-sectional shape and said first elliptical cross-sectional shape, and wherein a second flow channel is define by second interstices between said second annular cross-sectional shape and said second elliptical cross-sectional shape.

23. The multipolar, multi-lumen, virtual-electrode catheter of claim 22, wherein said first annular cross-sectional shape has a first outside diameter, wherein said second annular cross-sectional shape has a second outside diameter, wherein said first elliptical cross-sectional shape has a first minor axis length, wherein said second elliptical cross-sectional shape has a second minor axis length, wherein said first outside diameter matches said first minor axis length, and wherein said second outside diameter matches said second minor axis length.

24. The multipolar, multi-lumen, virtual-electrode catheter of claim 23, wherein said first flow channel comprises a first pair of crescent-moon-shaped regions and a first circular central region, and wherein said second flow channel comprises a second pair of crescent-moon-shaped regions and a second circular central region.

25. The multipolar, multi-lumen, virtual-electrode catheter of claim 1 further comprising at least one temperature sensor on said outer surface of said catheter body next to said at least one surface electrode.

26. The multipolar, multi-lumen, virtual-electrode catheter of claim 25, wherein said at least one temperature sensor is selected from the group consisting of a thermocouple, a thermister, and a fiber optic sensor.

27. The multipolar, multi-lumen, virtual-electrode catheter of claim 1, wherein said at least one surface electrode comprises
   a first outboard thermally-and-electrically-conductive surface electrode coil mounted on said outer surface of said catheter body,
   a second outboard thermally-and-electrically-conductive surface electrode coil mounted on said outer surface of said catheter body, and
   an intermediate thermally-and-electrically-conductive surface electrode coil mounted on said outer surface of said catheter body; and
wherein said virtual-electrode catheter further comprises
   a first longitudinally-extending temperature sensor that extends within said first outboard thermally-and-electrically-conductive surface electrode coil;
   a second longitudinally-extending temperature sensor that extends within said second outboard thermally-and-electrically-conductive surface electrode coil; and
   a third longitudinally-extending temperature sensor that extends within said intermediate thermally-and-electrically-conductive surface electrode coil.

28. The multipolar, multi-lumen, virtual-electrode catheter of claim 1, wherein said first and second internal electrodes are each selected from the group consisting of a coil electrode, a wire strand electrode, and a tubular electrode.

29. The multipolar, multi-lumen, virtual-electrode catheter of claim 1,
   wherein each of said first and second internal lumens has an elliptical transverse cross section with a minor axis;
   wherein each of said first and second internal electrodes comprises a coil electrode having a circular transverse cross section with an outer diameter; and
   wherein a length of said outer diameter of said first and second internal electrodes matches a length of said minor axes of said first and second internal lumens, thereby creating a first fluid channel in said first internal lumen and creating a second fluid channel in said second internal lumen, wherein each of said first and second flow channels comprises a pair of crescent-moon-shaped regions and a circular region.

30. The multipolar, multi-lumen, virtual-electrode catheter of claim 1, wherein said first internal electrode comprises a first small internal coil extending longitudinally within said first longitudinally-extending internal lumen, wherein said second internal electrode comprises a second small internal coil extending longitudinally within said second longitudinally-extending internal lumen, wherein said first small internal coil is partially embedded in an internal sidewall of said first longitudinally-extending internal lumen, and wherein said second small internal coil is partially embedded in an internal sidewall of said second longitudinally-extending internal lumen.

31. The multipolar, multi-lumen, virtual-electrode catheter of claim 1 further comprising a terminal body mounted at a distal end of said catheter body, wherein said first internal electrode further comprises a distal projection anchored to said terminal body, and wherein said second internal electrode further comprises a distal projection anchored to said terminal body.

32. The multipolar, multi-lumen, virtual-electrode catheter of claim 31, wherein said terminal body is a terminal sphere.

33. The multipolar, multi-lumen, virtual-electrode catheter of claim 1, wherein said catheter body further defines a third longitudinally-extending internal lumen adapted to slippingly receive a rail adapted to facilitate steering and shaping said catheter body.

34. A multipolar, multi-lumen, virtual-electrode catheter for performing radiofrequency ablation of cardiac tissue, the catheter comprising
   a catheter body defining an outer surface, a first internal lumen, and a second internal lumen, wherein said first and second internal lumens are adapted to carry conductive fluid;
   at least three metal electrodes positioned on said outer surface of said catheter body, wherein said at least three metal electrodes are adapted for placement against the cardiac tissue;
   a first metal conductor positioned within said first internal lumen and adapted to impart radiofrequency energy to the conductive fluid;
   a second metal conductor positioned within said second internal lumen and adapted to impart radiofrequency energy to the conductive fluid;
   a first opening on said outer surface of said catheter, said first opening adapted to create a flow path for the conductive fluid in said first internal lumen to flow out of the catheter and impinge upon the cardiac tissue as a virtual-electrode;
   a second opening on said outer surface of said catheter, said second opening adapted to create a flow path for the conductive fluid in said second internal lumen to flow out of the catheter and impinge upon the cardiac tissue as a virtual-electrode; and
   at least one temperature sensor on said outer surface of said catheter body in close juxtaposition to at least one of said at least three metal electrodes.

35. A method for tissue ablation using a multipolar, multi-lumen, virtual-electrode catheter comprising
   a catheter body with a sidewall and an outer surface;
   a first internal lumen extending within said catheter body and adapted to flowingly receive a conductive fluid;
   a second internal lumen extending within said catheter body and adapted to flowingly receive said conductive fluid;
   a first exit feature comprising a flow path from said first internal lumen through said catheter body sidewall to said catheter outer surface, said first exit feature being adapted to permit the conductive fluid to exit from said first internal lumen toward the tissue;

a second exit feature comprising a flow path from said second internal lumen through said catheter body sidewall to said catheter outer surface, said second exit feature being adapted to permit the conductive fluid to exit from said second internal lumen toward the tissue;

a first internal flexible conductor mounted within said first internal lumen adjacent to said first exit feature and to a first inner surface of said catheter body sidewall, wherein said first internal flexible conductor is adapted to deliver ablation energy to the tissue via the conductive fluid in said first internal lumen;

a second internal flexible conductor mounted within said second internal lumen adjacent to said second exit feature and to a second inner surface of said catheter body sidewall, wherein said second internal flexible conductor is adapted to deliver ablation energy to the tissue via the conductive fluid in said second internal lumen; and at least one surface electrode mounted on said outer surface of said catheter body adjacent to at least one of said first and second exit features;

the method comprising the steps of (a) flowing the conductive fluid within said first and second internal lumens and out of said first and second exit features;

(b) delivering ablation energy to said first and second internal flexible conductors;

(c) generating an electric field between at least one of said first and second internal flexible conductors and said at least one surface electrode; and (d) terminating delivery of said ablation energy upon creating of a lesion in the tissue.

36. A method for tissue ablation using a multipolar, multi-lumen, virtual-electrode catheter, the method comprising the steps of (a) placing against the tissue at least one of a first outboard dispersive surface electrode, a second outboard dispersive surface electrode, and an intermediate dispersive surface electrode, wherein said first outboard dispersive surface electrode, said second outboard dispersive surface electrode, and said intermediate dispersive surface electrode are each mounted on an outer surface of a catheter body of the virtual-electrode catheter;

(b) flowing a conductive fluid through a first internal lumen and a second internal lumen, both said internal lumens extending within said catheter body toward at least one exit feature that is adjacent to at least one of said first outboard dispersive surface electrode, said second outboard dispersive surface electrode, and said intermediate dispersive surface electrode;

(c) delivering ablation energy to at least one of a first active internal flexible conductor within said first internal lumen, and a second active internal flexible conductor within said second internal lumen;

(d) generating at least one concentrated electric field between at least one of said first and second internal flexible conductors, and at least one of said first outboard dispersive surface electrode, said second outboard dispersive surface electrode, and said intermediate dispersive surface electrode; and (e) terminating delivery of said ablation energy after creation of a lesion in the tissue.

37. A method for tissue ablation using a multipolar, multi-lumen, virtual-electrode catheter, the method comprising the steps of setting up a first virtual electrode comprising an ablative energy source, a first internal electrode, a first exit feature, and conductive fluid flowing along said first internal electrode and through said first exit feature;

setting up a second virtual electrode comprising said ablative energy source, a second internal electrode, a second exit feature, and conductive fluid flowing along said second internal electrode and through said second exit feature;

placing each of a first outboard surface electrode, a second outboard surface electrode, and an intermediate surface electrode against tissue to be ablated;

activating said first virtual electrode, thereby establishing a first electric field that extends between said first exit feature and said first outboard surface electrode, wherein said first electric field passes through the tissue; and establishing a second electric field that extends between said first exit feature and said intermediate surface electrode, wherein said second electric field passes through the tissue;

activating said second virtual electrode, thereby establishing a third electric field that extends between said second exit feature and said intermediate surface electrode, wherein said third electric field passes through the tissue; and establishing a fourth electric field that extends between said second exit feature and said second outboard surface electrode, wherein said fourth electric field passes through the tissue; and maintaining at least one of said first, second, third, and fourth electric fields until a lesion is created in the tissue.

* * * * *